US005883074A

United States Patent [19]
Boggs et al.

[11] Patent Number: 5,883,074
[45] Date of Patent: Mar. 16, 1999

[54] POTENTIATORS OF ANTIBACTERIAL AGENTS

[75] Inventors: Amy Boggs, Menlo Park; Joaquim Trias, San Mateo; Scott Hecker, Los Gatos, all of Calif.

[73] Assignee: Microcide Pharmaceuticals, Inc., Mountainview, Calif.

[21] Appl. No.: 388,109

[22] Filed: Feb. 8, 1995

[51] Int. Cl.$^6$ .......................... A61K 31/43; A61K 31/71; A61K 38/12; A61K 38/14

[52] U.S. Cl. .................................. 514/8; 514/11; 514/29; 514/37; 514/39; 514/152; 514/153; 514/154; 514/197; 514/198; 514/199; 514/312

[58] Field of Search ........................... 435/32, 33; 514/8, 514/9, 11, 197, 198, 199, 729, 730, 29, 37, 39, 152, 153, 154, 312, 182, 510, 719, 721; 568/808, 819

[56] References Cited

U.S. PATENT DOCUMENTS

| | | | |
|---|---|---|---|
| 2,809,996 | 10/1957 | Stoll | 568/445 |
| 3,792,167 | 2/1974 | Fried et al. | |
| 3,898,330 | 8/1975 | McGinty | 514/39 |
| 3,940,478 | 2/1976 | Kurtz | 424/94.64 |
| 4,134,972 | 1/1979 | Atherton et al. | 514/7 |
| 4,153,686 | 5/1979 | Nagel | 530/395 |
| 4,560,553 | 12/1985 | Zupan | 514/23 |
| 4,621,137 | 11/1986 | Miyake et al. | 536/6.3 |
| 5,198,419 | 3/1993 | Ando et al. | 530/832 |
| 5,221,664 | 6/1993 | Berkowitz et al. | 514/6 |
| 5,277,907 | 1/1994 | Loria | 435/240.2 |
| 5,358,752 | 10/1994 | Evans et al. | 424/450 |
| 5,453,276 | 9/1995 | Nakatsu et al. | 424/405 |
| 5,478,819 | 12/1995 | Tarpila et al. | 514/199 |
| 5,543,417 | 8/1996 | Waldstreicher | 514/284 |
| 5,587,358 | 12/1996 | Sukigara et al. | 514/11 |
| 5,616,568 | 4/1997 | Pouyani et al. | 514/54 |
| 5,646,023 | 7/1997 | Secor et al. | 435/172.3 |

FOREIGN PATENT DOCUMENTS 8912399 12/1989 WIPO.

OTHER PUBLICATIONS

Chemical Abstracts 101:3824 m (Jul. 2, 1984).
Kirk–Othmer Encyclopedia of Chemical Technology, 3rd ed. New York: John Wiley & Sons, vol. 22, p. 753, 1983.
The Merck Index, 10$^{th}$ ed. Rahway: Merck & Co., Inc. pp. 248, 631, 758, 759, 1259, 1983.
Piccinini et al. Effect of terpenes on The Cell Permeability . . . Advances in Antimicrobial and Antineoplastic Chemotherapy. pp. 855–857, 1972.
Allen et al. 7–Hydroxytropolone: an Inhibitor of Aminoglycoside . . . Antimicrobial Agents and Chemotherapy, Nov. 1982, vol. 22, No. 5, pp. 824–831.
Smith et al. Effects of Intravitreal Dexamethasone on Concentration . . . Antimicrobial Agents and Chemotherapy, Jul. 1991, vol. 35, No. 7, pp. 1298–1302.
Arthur & Courvalin, "Genetics and Mechanisms of Glycopeptide Resistance in Enterococci," *Antimicrob. Agents Chemother.* 37:1563–1571 (1993).
Berger–Bachi and Kohler, *FEMS Microbiol. Lett.* 20:305–309 (1983).
Blickenstaff et al., "Total Synthesis of Steroids," *Organic Chemistry* vol. 30, 1974 (Table of Contents).
Bryan and Godfrey, "β–Lactam Antibiotics: Mode of Action and Bacterial Resistance, Ch. 16" in *Antibiotics in Laboratory Medicine*, 3rd Ed., Lorian ed. pp. 599–663 (1991).
Chambers, "Methicillin–Resistant Staphylococci," *Clin. Microb. Rev.* 1:173–186 (1988).

(List continued on next page.)

*Primary Examiner*—Jeffrey E. Russel
*Attorney, Agent, or Firm*—Lyon & Lyon LLP

[57] ABSTRACT

Methods for screening for compounds which potentiate the activity of antibacterial agents against bacteria resistant to the antibacterial agent alone, pharmaceutical compositions including such potentiators, and methods of treating bacterial infections using a combination of a potentiator and a potentiated antibacterial agent, which are useful for overcoming the resistance of a bacterial strain for an antibacterial agent.

55 Claims, 18 Drawing Sheets

| Potentiator | Structure | Methicillin MIC (μg/ml) for Col* | Potentiator | Structure | Methicillin MIC (μg/ml) for Col* |
|---|---|---|---|---|---|
| 2-Hydroxy-8-methoxy-4a-methyl-1,2,3,4,4a,4b,5,6,10b,11,12,12a-dodecahydrochrysene | 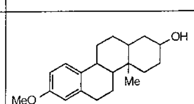 | 32 | 5β-androstan-3β-ol | 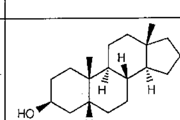 | 8 |
| 5α-androstan-3β-ol | 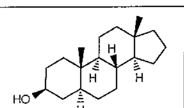 | 8 | α-estradiol | 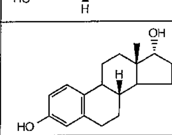 | 256 |
| 5β-androstan-3α-ol | 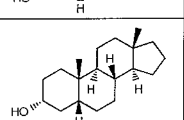 | 16 | β-estradiol | 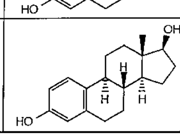 | 512 |

OTHER PUBLICATIONS

Collins et al., "Immunoglobulin G: Potentiation of Tobramycin and Azlocillin in the Treatment of *Pseudomonas aerugionsa* Sepsis in Neutropenic Mice and Neutralization of Exotoxin A in Vivo," *Review Infect. Dis.* 8:S420–S425 (1986).

De Jonge et al., "Altered Muropeptide Composition in *Staphylococcus aureus* Strains with an Inactivated femA Locus," *J. Bacteriol.* 17:2779–2782 (1993).

De Lencastre et al., "Molecular aspects of methicillin resistance in *Staphylococcus aureus,*" *J. Antimicrob. Chemother.* 33:7–24 (1994).

Donowitz and Mandell, "Beta–Lactam Antibiotics," *N. Engl. J. Med.* 318:419–426 (1988).

Elion et al., "Antagonists of Nucleic Acid Derivatives. VIII. Synergisms in Combinations of Biochemically Related Antimetabolites," *J. Biol. Chem..* 208:477–488 (1954).

Eliopolous & Moellering, "Ch. 13—Antimicrobial Combinations," in *Antibiotics in Laboratory Medicine,* 3rd ed., Lorian ed., at pp. 434–441 (1991).

Fontana et al., *Antimicrob. Agents and Chemother.* 38:1980–1983 (1994).

Gustafson et al., "The femC Locus of *Staphylococcus aureus* Required for Methicillin Resistance Includes the Glutamine Synthetase Operon," *J. Bacteriol.* 176:1460–1467 (1994).

Hartman and Tomasz, "Expression of Methicillin Resistance in Heterogeneous Strains of *Staphylococcus aureus,*" *Antimicrob. Agents Chemother.* 29:85–92 (1986).

Henze et al., "Influence of femB on Methicillin Resistance and Peptidoglycan Metabolism in *Staphylococcus auerus,*" *J. Bacteriol.* 175:1612–1620 (1993).

Kornblum et al., *Eur. J. Clin. Microbiol.* 5:714–718 (1986).

Leclercq et al., *N. Engl. J. Med.* 319:157–161 (1988).

Lencastre & Tomasz, *Antimicrob. Agents Chemother.* 38:2590–2598 (1994).

Lorian, *Antibiotics in Laboratory Medicine,* 3rd ed., pp. 72–78 (1991).

Maidhof et al., "femA, Which Encodes a Factor Essential for Expression of Methicillin Resistance, Affects Glycine Content of Petpidoglycan in Methicillin–Resistant and Methicillin–Susceptible *Staphylococcus aureus* Strains," *J. Bacteriol.* 173:3507–3513 (1991).

Murakami and Tomasz, "Involvement of Multiple Genetic Determinants in High–Level Methicillin Resistance in *Staphylococcus aureus,*" *J. Bact.* 171:874–879 (1989).

Murakami et al., "Production of Low–Affinity Penicillin–Binding Protein by Low– and High–Resistance Groups of Methicillin–Resistant *Staphylococcus aureus,*" *Antimicrob. Agents Chemother.* 31:1307–1311 (1987).

NCCLS publication entitled Methods for Dilution Antimicrobial Susceptibility Tests (1991).

Neu, "The Crisis in Antibiotic Resistance," *Science* 257:1064–1073 (1992).

Ryffel et al., *Antimicrob. Agents Chemother.* 38: 724–728 (1994).

Uttley et al., *Epidemiol. Infect.* 103:173–181 (1989).

Vogelman et al., "In Vivo Postantibiotic Effect in a Thigh Infection in Neutropenic Mice," *J. Infect. Dis.* 157:287–298 (1988).

Williamson et al., *J. Gen. Microbiol.* 131:1933–1940, 1985.

Luckner, "Ch. 5—The biosynthesis of secondary natural products from activated isoprene," *Secondary metabolism in plants and animals,* translated by Mr. T.N. Vasudevan, Academic Press, N.Y., pp. 122–163 (1972).

FIG. 2.

| | MIC(ug/ml) for Col (MRSA) | | | SUSCEPTIBILITY BREAKPOINTS † |
|---|---|---|---|---|
| LARIXOL ACETATE (ug/ml) | 0 | 5 | 10 | |
| PENICILLINS | | | | |
| AMPCILLIN | 16 | 8 | 0.5 | ≤8 |
| CLOXAXILLIN | 512 | 16 | 0.5 | N/A |
| METHICILLIN | 1024 | 256 | 8 | ≤8 |
| OXACILLIN | 256 | 128 | 0.5 | ≤2 |
| PIPERACILLIN | 128 | 128 | 2 | N/A |
| CEPHALOSPORINS & OTHER CEPHEMS | | | | |
| CEFACLOR | 128 | 64 | 4 | ≤8 |
| CEFAMANDOLE | 16 | 16 | 1 | ≤8 |
| CEFAZOLIN | 256 | 128 | 0.125 | ≤8 |
| CEFOPERAZONE | 1024 | 1024 | 8 | ≤16 |
| CEFOTAXIME | 1024 | 1024 | 8 | ≤8 |
| CEFOXITIN | 256 | 128 | 16 | ≤8, 16: intermediate |
| CEFTAZIDIME | 256 | 256 | 4 | ≤8 |
| CEFTRIAXONE | >1024 | >1024 | 32 | ≤8, 16-32: intermediate |
| CEPHALOTHIN | 64 | 64 | 0.25 | ≤8 |
| CARBAPENEMS | | | | |
| IMIPENEM | 32 | 16 | 0.03 | ≤4 |
| GLYCOPEPTIDES | | | | |
| VANCOMYCIN | 1 | 0.5 | 0.5 | ≤4 |
| AMINOGLYCOSIDES | | | | |
| GENTAMICIN | 0.5 | 0.5 | 0.5 | ≤4 |

\*MICs were determined in the presence of 0, 5, and 10 ug/ml Larixol acetate. Cell density was determined by absorbance at 600 nm.

†As defined by NCCLS for each antibiotic used alone against *S. aureus*

Imipenem Potentiation by Larixol acetate

Imipenem MICs, with and without 10 ug/ml of Larixol acetate, were run vs. 5 MRSA strains to ascertain the potentiation effect of this compound. The MIC was run in the microtiter plate format using standard techniques.

The following MRSA strains were used:
1- MRSA Col
2- MRSA Col 2278 (inducible β-lactamase and methicillin resistance).
3- MRSA Sa 038 - clinical isolate
4- MRSA Spain 356 - clinical isolate; multiply resistant
5- MRSA Spain 195 - clinical isolate; multiply resistant Results:

MIC (ug/ml)

| organism: | Imipenem MIC | imipenem+Larixol acetate MIC |
|---|---|---|
| Col | 64 | 0.06 |
| Col 2278 | >64 | 0.06 |
| sa 038 | 64 | 2 |
| Spain 356 | >64 | 0.5 |
| Spain 195 | >64 | 0.06 |

Larixol acetate showed a marked potentiation effect vs the strains tested. The compound showed no antimicrobial activity when tested alone against these strains.

| Potentiator (μg/ml) | Methicillin MIC* (ug/ml) for Col8A (MSSA) | | | Methicillin MIC* (ug/ml) for Col (MRSA) | | | Methicillin MIC* (ug/ml) for Strain76 (MRSA) | | |
|---|---|---|---|---|---|---|---|---|---|
| | 0 | 5 | 10 | 0 | 5 | 10 | 0 | 5 | 10 |
| HMM-dodecahydrochrysene (lead compound from methicillin potentiation screen) | 1 | 1 | 1 | 512 | 32 | 16 | 128 | 16 | 8 |
| 5α-androstan-3β-ol | 1 | 1 | 1 | 256 | 8 | 8 | 128 | 32 | 32 |
| 5β-androstan-3α-ol | 2 | 2 | 4 | 256 | 16 | 16 | 256 | 16 | 16 |
| 5β-androstan-3β-ol | 2 | 2 | 2 | 256 | 8 | 16 | 128 | 8 | 16 |
| α-estradiol | 2 | 1 | 2 | 256 | 256 | 256 | 256 | 256 | 256 |
| β-estradiol | 1 | 2 | 2 | 512 | 512 | 512 | 256 | 128 | 64 |
| β-estradiol 3-methyl ether | 1 | 1 | 1 | 512 | 64 | 16 | 256 | 32 | 16 |
| 008-149 | 1 | 1 | 1 | 256 | 64 | 4 | 64 | 16 | 8 |
| Epiandrosterone | 1 | 1 | 1 | 256 | 256 | 128 | 128 | 128 | 32 |
| Ergocalciferol | 1 | 1 | 1 | 256 | 128 | 64 | 128 | 128 | 128 |

* Methicillin MICs were determined in the presence of 0, 5, and 10 ug/ml of MC200520 or analogs. Cell density was determined by absorbance at 600 nm.

FIG. 5b.

| Potentiator (ug/ml) | Methicillin MIC* (ug/ml) for Col8A (MSSA) | | | Methicillin MIC* (ug/ml) for Col (MRSA) | | | Methicillin MIC* (ug/ml) for Strain76(MRSA) | | |
|---|---|---|---|---|---|---|---|---|---|
| | 0 | 5 | 10 | 0 | 5 | 10 | 0 | 5 | 10 |
| HMM-dodecahydrochrysene (lead compound from methicillin potentiation screen) | 1 | 1 | 1 | 512 | 32 | 16 | 128 | 16 | 8 |
| 6-methoxy-1,2,3,4-tetrahydronaphthalene | 2 | 2 | 2 | 512 | 512 | 512 | 128 | 128 | 128 |
| 6,7-Dimethoxy-1-tetralone | 2 | 2 | 2 | 512 | 512 | 512 | 256 | 256 | 256 |
| 6-methoxy-1-tetralone | 2 | 2 | 2 | 512 | 512 | 512 | 512 | 512 | 512 |
| Dextromethorphan | 2 | 2 | 2 | 512 | 512 | 512 | 128 | 512 | 512 |
| Methyl O-methyl-podocarpate | 2 | 2 | 2 | 512 | 512 | 512 | 256 | 256 | 512 |

* Methicillin MICs were determined in the presence of 0, 5, and 10 ug/ml of MC200520 or analogs. Cell density was determined by absorbance at 600 nm.

FIG. 5C

| Potentiator (ug/ml) | Methicillin MIC (ug/ml) for Col8A (MSSA) | | | Methicillin MIC (ug/ml) for Col (MRSA) | | | Methicillin MIC (ug/ml) for Strain76 (MRSA) | | |
|---|---|---|---|---|---|---|---|---|---|
| | 0 | 5 | 10 | 0 | 5 | 10 | 0 | 5 | 10 |
| Larixol acetate (lead compound from methicillin potentiation screen) | 1 | 1 | 0.5 | 128 | 8 | 4 | 128 | 16 | 4 |
| (-)-Ambroxide | 1 | 2 | 2 | 512 | 512 | 64 | 256 | 128 | 64 |
| (3aR)-(+)-Sclareolide | 1 | 2 | 2 | 512 | 512 | 128 | 128 | 512 | 64 |
| 10A,12A-Dimethyl-8-Hydroxy-Tetradecahydrochrysene | 1 | 1 | 1 | 512 | 8 | 8 | 256 | 8 | 8 |
| 4A,5Epoxy-3-Oxo-14H-4,6A,9,9-4Me-Phenanthro (2,3-D)(1,3)Dioxole-4-Propionic acid | 1 | 1 | 1 | 512 | 512 | 512 | 256 | 512 | 256 |
| Andrographolide | 1 | 1 | 2 | 512 | 512 | 512 | 512 | 512 | 512 |
| 7Alpha-Hydroxymanool | 1 | 1 | 1 | 512 | 256 | 32 | 256 | 256 | 128 |
| Ursolic acid | 1 | (tox)† | (tox) | 512 | (tox) | (tox) | 256 | (tox) | (tox) |
| Uvaol | 1 | 1 | 2 | 512 | 16 | 16 | 256 | 128 | 128 |

* Methicillin MIC were determined in the presence of 0, 5, and 10 ug/ml of MC200616 or analogs. Cell density was determined by absorbance at 600 nm.
† This compound shows intrinsic antibacterial activity (fails criterion #2).

FIG. 6a.

| Potentiator | Structure | Methicillin MIC (µg/ml) for Col* | Potentiator | Structure | Methicillin MIC (µg/ml) for Col* |
|---|---|---|---|---|---|
| 2-Hydroxy-8-methoxy-4a-methyl-1,2,3,4,4a,4b,5,6,10b,11,12,12a-dodecahydrochrysene | | 32 | 5β-androstan-3β-ol | | 8 |
| 5α-androstan-3β-ol | 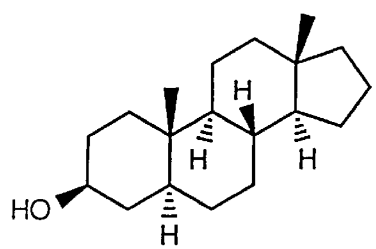 | 8 | α-estradiol | 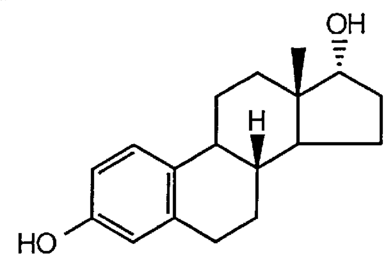 | 256 |
| 5β-androstan-3α-ol | 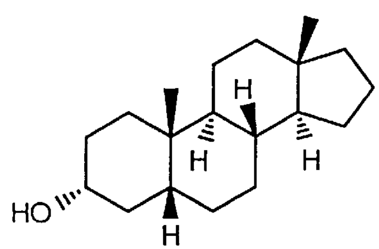 | 16 | β-estradiol | 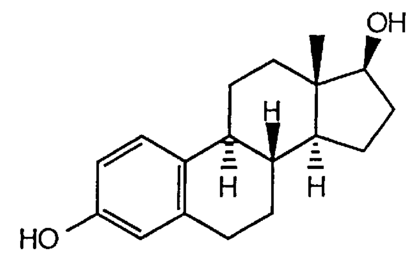 | 512 |

FIG. 6b.

| Potentiator | Structure | Methicillin MIC (μg/ml) for Col* | Potentiator | Structure | Methicillin MIC (μg/ml) for Col* |
|---|---|---|---|---|---|
| β-estradiol 3-methyl ether | 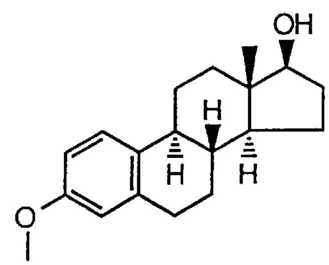 | 64 | Epiandrosterone | 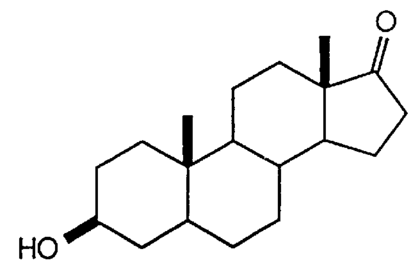 | 256 |
| Epiandrosterone acetate | | 32 | Ergocalciferol | | 128 |

FIG. 6c.

| Potentiator | Structure | Methicillin MIC (μg/ml) for Col* | Potentiator | Structure | Methicillin MIC (μg/ml) for Col* |
|---|---|---|---|---|---|
| 2-Hydroxy-8-methoxy-4a-methyl-1,2,3,4,4a,4b,5,6,10b,11,12,12a-dodecahydrochrysene | | 32 | 6-methoxy-1-tetralone | | 512 |
| 6-methoxy-tetrahydro-naphthalene | 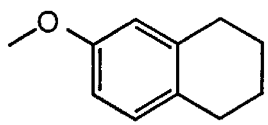 | 512 | Dextro-methorphan | 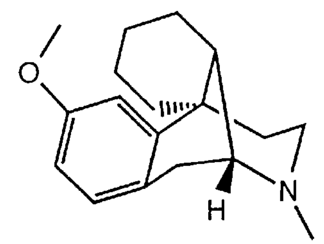 | 512 |
| 6,7-Dimethoxy-1-tetralone | 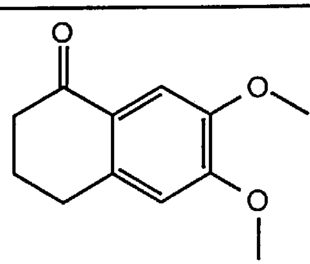 | 512 | Methyl O-methyl-podocarpate | 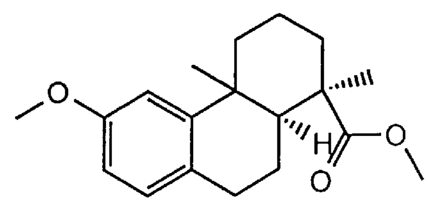 | 512 |

FIG. 6d.
| Potentiator | Structure | Methicillin MIC (μg/ml) for Col with 5 μg/ml of potentiator |
|---|---|---|
| Larixol acetate | 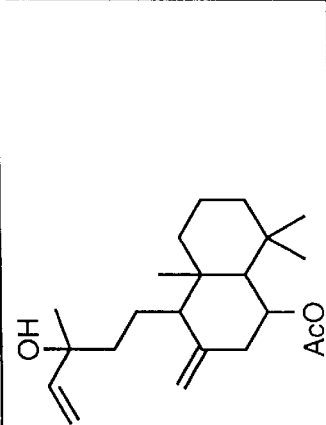 | 8 |
| 10A,12A-Dimethyl-8-Hydroxy-Tetradecahydrochrysene | 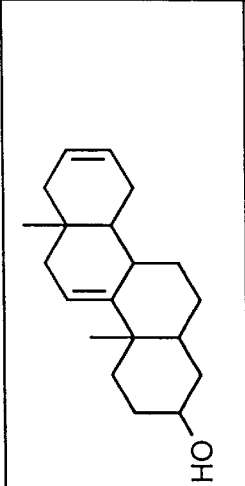 | 8 |
| Uvaol | 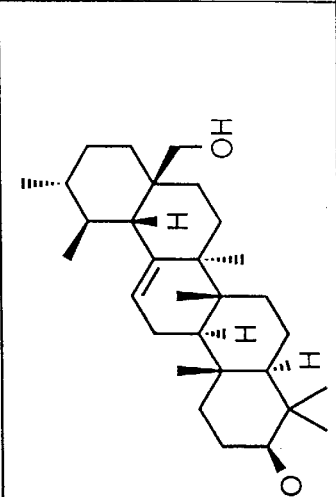 | 16 |

FIG. 6e
| Potentiator | Structure | Methicillin MIC (μg/ml) for Col with 5 μg/ml of potentiator |
|---|---|---|
| (-)-Ambroxide | 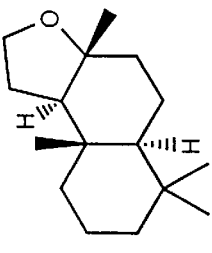 | 512 |
| 4A,5Epoxy-3-Oxo-14H-4,6A,9,9-4Me-Phenanthro (2,3-D)(1,3)Dioxole-4-Propionic acid | 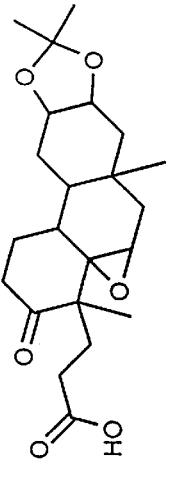 | 512 |
| Andrographolide | 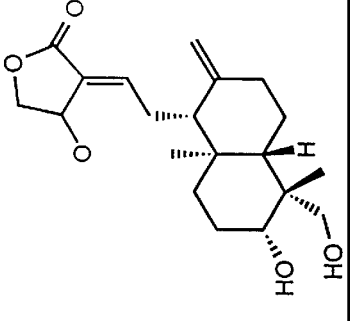 | 512 |

FIG. 6f.
| Potentiator | Structure | Methicillin MIC (µg/ml) for Col with 5 µg/ml of potentiator |
|---|---|---|
| 7Alpha-Hydroxymanool | 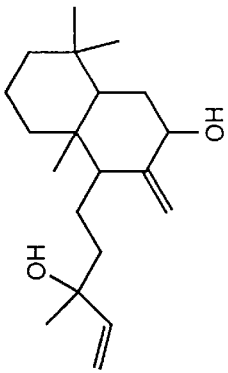 | 256 |
| Ursolic acid | 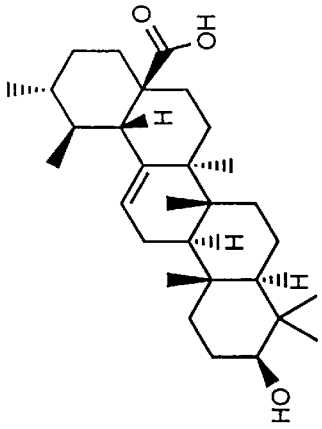 | N/A |
| (3aR)-(+)-Sclareolide | 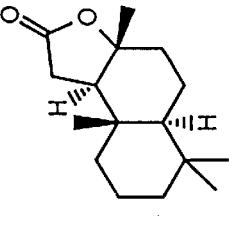 | 512 |

FIG. 8.
6-ethyl-7-[1-oxo-3-(1-pyrrolidino)]propyl-1,2,3,4-tetrahydro-1,1,4,4-tetramethylnaphthalene
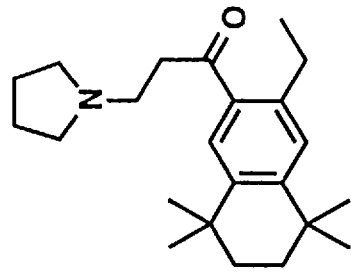
96/36, 100/33
49/26, 59/24
brazilin
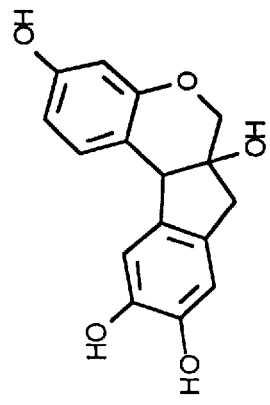
75/32, 72/32
74/20, 36/21
N-benzyl thiosalicylamide
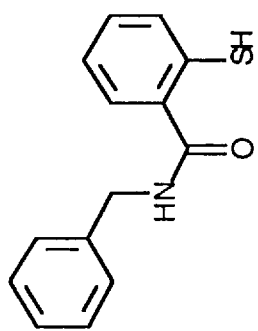
VPS-20    88/4, 98/1.5
VPS-D-Ala  4/9, 98/0

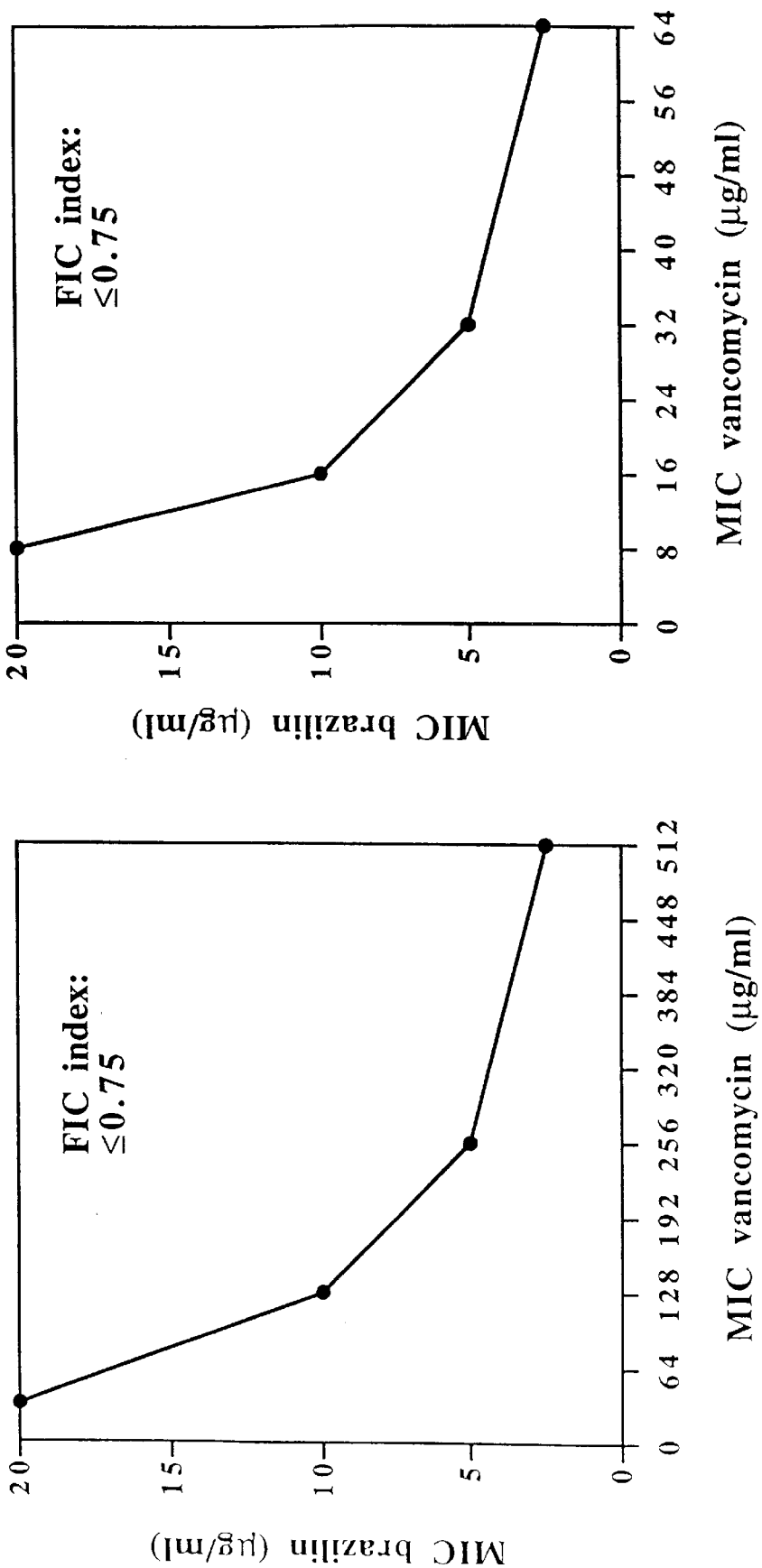

POTENTIATORS OF ANTIBACTERIAL AGENTS

FIELD OF THE INVENTION

This invention relates to the fields of antibacterial treatments and compositions for such treatments. It further relates to methods of screening to identify compounds which are potentiators of antibacterial therapeutic agents.

BACKGROUND OF THE INVENTION

During the past 30 years a large number of antimicrobial agents of a number of different structural classes have been developed and used in treating bacterial infections. Important among these structural classes are the β-lactams, glycopeptides, macrolides, quinolones, tetracyclines, and aminoglycosides. Of these, the β-lactams include a large number of agents, and their mechanism of action has been studied in considerable depth.

β-lactam antibacterial agents are generally effective antibacterial agents of relatively low toxicity (Donowitz and Mandell, 318 *N. Engl. J. Med.* 419–26 (1988)). β-lactam agents contain the β-lactam ring structure, and include e.g., penicillins, cephalosporins, carbacephems, carbapenems, penems, and monobactams. The β-lactam agents kill bacteria by binding to specific target proteins in the cytoplasmic membranes of bacteria. When bound to the target proteins, the β-lactam agents prevent biosynthesis of bacterial cell walls. These target proteins can be identified by their ability to covalently bind an isotopically-labeled β-lactam, such as penicillin, and are termed penicillin-binding proteins (PBPs). The enzymatic functions of higher molecular weight PBPs are essential in the cross-linking of peptidoglycan in the bacterial cell wall. The antibacterial effects of the β-lactam antibacterial agents arise from their ability to act as substrate analogs of the acyl-D-alanyl-D-alanine component of peptidoglycan. By acting as substrate analogs, the β-lactam agents bind to and inhibit the enzymatic activity of high molecular weight PBPs, resulting in the inhibition of peptidoglycan synthesis. (Bryan and Godfrey, β-lactam Antibodies: Mode of Action and Bacterial Resistance, Ch. 16 in *Antibacterial Agents in Laboratory Medicine,* 3rd Ed., Lorian ed. at 599–663 (1991)). The inhibition of synthesis of the rigid peptidoglycan layer usually causes the death of the bacteria because the rigid peptidoglycan layer is needed to maintain the integrity of the inner cytoplasmic membrane of the bacteria under conditions of low osmolarity. Thus, without a properly synthesized peptidoglycan layer, bacteria can swell and burst or, in cases where the PBPs are partially inhibited, the cells can exhibit filamentous growth leading to fragmentation.

Because of this ability to inhibit bacterial peptidoglycan synthesis, β-lactam antibacterial agents have been highly effective and widely used to treat bacterial infections; however, mutant strains of bacteria which are resistant to the β-lactam agents are encountered with increasing frequency. In particular, many strains of Staphylococcus aureus are developing increasing resistance to available antibacterial agents (the so-called methicillin resistant *Staphylococcus aureus* (MRSA)); such resistance is also present in strains of *Staphylococcus epidermidis* (MRSE).

There are three major mechanisms of bacterial resistance to β-lactam agents. In many cases the resistance is due to the presence of a β-lactamase which inactivates β-lactam drugs by cleaving the β-lactam ring. In addition, in gram-negative bacteria, resistance can be attained by a reduced cell permeability to β-lactam agents. A third mode of β-lactam resistance is alteration of the target of antibiotic action by structural modification or acquisition of a PBP which has a reduced binding affinity for the antibacterial agent. Although some of the organisms exhibiting this mode of resistance do not normally also produce a β-lactamase, the MRSA often possess both resistance mechanisms.

Methicillin is a β-lactamase stable β-lactam antibacterial agent often used for the treatment of infections arising from β-lactamase-producing strains of Staphylococcus aureus. However, the incidence of MRSA infections has become a serious problem (Chambers, *Clin. Microb. Rev.* 1:173–186 (1988); Neu, H., *Science* 257:1064–1073 (1992); De Lencastre et al., *J. Antimicrob. Chemother.* 33:7–24 (1994)). In fact, the current average incidence of MRSA in some large hospitals in the United States increased from 8% in 1986 to 40% in 1992.

Methicillin resistance is generally thought to be mediated by the resistance factor PBP2a, a 78-kDa PBP which has reduced affinity for β-lactams, including methicillin. It is postulated that PBP2a compensates for the other inhibited PBPs in the presence of β-lactam drugs, allowing continued peptidoglycan synthesis in the presence of β-lactams (De Lencastre et al., supra, 1994).

In addition to the resistance factor PBP2a, there are several accessory factors involved in the expression of methicillin resistance in *S. aureus*. Included in this category are the fem gene products (Berger-Bachi and Kohler, *FEMS Microbiol. Lett.* 20: 305–309 (1983); Hartman and Tomasz, *Antimicrob. Agents Chemother.* 29(1): 85–92 (1986); Kornblum et al., *Eur. J. Clin. Microbiol.* 5: 714–718 (1986); Murakami et al., *Antimicrob. Agents Chemother.* 31: 1307–1311 (1987)), and the chr* gene product (Ryffel et al., *Antimicrob. Agents Chemother.* 38: 724–728 (1994); see also Lencaster & Tomosz, *Antimicrob. Agents Chemother.* 38:2590–2598 (1994)). Insertional inactivation of these genes in PBP2a-producing MRSA strains results in greater susceptibility to methicillin. The fem factors appear to be involved in the synthesis of peptidoglycan (Henze, et al., *J. Bacteriol.* 175(6): 1612–1620 (1993); De Jonge, et al., *J. Bacteriol.* 175(9): 2779–2782 (1993); Gustafson, et al., *J. Bacteriol.* 176(5): 1460–1467 (1994)).

Furthermore, MRSA have demonstrated the ability to rapidly develop resistance as new antibacterial agents become available. In the mid 1980s, new fluoroquinolone antimicrobial agents were developed, including ciprofloxacin, but the initial effectiveness of these compounds against staphylococci was short-lived. A study by the Centers for Disease Control showed that ciprofloxacin resistance of MRSA increased from less than 5% to greater than 80% within 1 year. (Neu, supra).

There are now MRSA strains which are susceptible to only a single class of clinically available antibacterial agents, the glycopeptides. Thus, there is a need for the development of new, efficient anti-MRSA treatments before resistance to glycopeptide antibacterial agents emerges in multi-resistant MRSA strains.

A mechanism for ampicillin resistance, similar to the mecA/PBP2a-mediated methicillin resistance in MRSA, has been observed in *Enterococcus faecium*. Such resistant strains produce a PBP (PBP5) which, like PBP2a in staphylococci, has low affinity for β-lactams, and which is thought to carry on peptidoglycan synthesis when other PBPs have been inhibited by β-lactams (Williamson et al., *J. Gen. Microbiol.* 131:1933–1940, 1985, Fontana et al., *Antimicrob. Agents and Chemother.* 38:1980–1983, 1994).

As with the β-lactams, glycopeptides such as vancomycin and teicoplanin have been used for many years to treat a variety of Gram-positive bacterial infections. Until 1986 there were no reports of acquired resistance to these antibacterial agents. At that time, two research groups discovered high-level resistance in clinically important Enterococci (Leclercq et al., *N. Engl. J. Med.* 319:157–161 (1988); Uttley et al., *Epidemiol. Infect.* 103:173–181 (1989)). The resistance factors were carried on plasmids transmissible to other Gram-positive bacteria. Transmission of the resistance mechanism to Staphylococci is possible (and likely in the future) though no clinical isolates of *S. aureus* have yet been confirmed. However, resistance to glycopeptides in the Enterococci is now very common, and isolates of Enterococci exist which are virtually untreatable, either with glycopeptides or with other antibacterial agents.

The mechanism of antibacterial activity of glycopeptides in susceptible bacteria differs from the mechanisms of most other antibiotics; rather than being enzyme inhibitors, the glycopeptides bind to a critical precursor in the cell wall synthesis process, masking the precursor and blocking subsequent steps in the process. Specifically, the glycopeptide binds to two terminal alanine residues in a peptidoglycan pentapeptide.

The mechanism of glycopeptide resistance in Enterococci is then due to the production of an alternative precursor for the cell wall synthesis process. In the most common example, the two terminal alanines of the pentapeptide are replaced by an alanine and a lactate moiety. Existing glycopeptides do not bind effectively to that altered peptide, resulting in resistance to the antibiotics.

The genetic basis of resistance to glycopeptides has been determined (Arthur & Courvalin, *Antimicrob. Agents Chemother.* 37:1563–1571 (1993)). In the clinically most important enterococci, *E. faecium* and *E. faecalis*, two principal phenotypes are observed (VanA, VanB). Both mechanisms lead to vancomycin resistance, but teicoplanin may still be effective against VanB isolates. The clinically less important enterococci, *E. gallinarum* and *E. casseliflavus* exhibit a third resistance phenotype (VanC), which is constitutively expressed (rather than being inducible) and is presumed to be chromosomally carried (rather than being located on a transmissible extragenic element).

The above material is not admitted to be prior art to the pending claims but is provided only to aid the understanding of the reader.

SUMMARY OF THE INVENTION

This invention relates to methods for screening compounds useful as potentiators of antibacterial agents, to compositions including such compounds, and to methods for treating bacterial infections using such compositions. We have found that small molecules (termed potentiators) can be found which exhibit little or no antibacterial activity when used alone and which are not primarily anti-β-lactamases, but which can induce susceptibility to an antibacterial agent in a bacterium resistant to that agent when the potentiator is used in conjunction with the antibacterial agent. (So the effect on susceptibility is not primarily due to anti-β-lactamase activity.) The PBP 2a mediated methicillin resistance in MRSA (essentially the same resistance mechanism is observed in methicillin resistant *Staphylococcus epidermidis* (MRSE)) illustrates that bacterial resistance to antimicrobial agents is often mediated by a number of different components of a bacterium. In MRSA/MRSE those components include PBP 2a and the fem gene products, and in *Enterococcus faecium* the components include PBP5 and related gene products. Thus, these potentiators can act by affecting one or more of the components mediating resistance in a bacterium. For example, in MRSA/MRSE, a potentiator can act by affecting PBP2a or the fem gene products, and in *Enterococcus faecium* a potentiator can act by affecting PBP5 and related products. By inhibiting or disabling an important resistance factor, the previously resistant organism then exhibits a methicillin- or ampicillin-susceptible phenotype, respectively, and can be treated with traditional antibacterial agent therapy. Similarly, potentiators can be found for antibacterial agents other than methicillin and ampicillin, and for other resistant bacteria (see, e.g., Example 11 herein).

By inducing a phenotype susceptible to an antibacterial agent, the potentiators thus enhance, or potentiate, the activity of antibacterial agents, e.g., β-lactam agents and β-lactam mimics. While this is particularly appropriate against resistant bacterial strains, it may also be appropriate in some cases in treating non-resistant strains. For example, if a bacterial population is heterogeneous, with a resistant sub-population, such treatment could prevent the emergence of that resistant sub-population. In addition, if a potentiator reduces the Minimum Inhibitory Concentration (MIC) of an antibacterial agent (where the MIC is the minimum concentration of antibacterial agent which will completely inhibit growth) in a susceptible strain, then such treatment may be advantageous to enable a reduction in the amount of antibacterial agent administered (could reduce side effects of an antibiotic), or to decrease the frequency of administration. Treatments using these potentiators thus represent a new approach to antibacterial therapy in which a potentiator can be administered together with an antibacterial agent (either simultaneously or serially) to allow effective treatment of an infection involving a resistant bacterium, or to reduce the amount of antibacterial agent necessary to treat an infection. This will therefore reduce the need to develop new antibacterial agents as bacteria develop resistance to known antibacterial agents. Instead, potentiators can be used to enhance the activity of antibacterial agents whose clinical efficacy has been limited by the increasing prevalence of resistant strains.

Thus, in a first aspect this invention provides methods of screening for potentiator compounds, comprising determining whether putative potentiator compounds inhibit the growth of a bacterium resistant to an antibacterial agent when said bacterium is grown in appropriate medium in the presence of a putative potentiator compound and a concentration of the antibacterial agent below the MIC of that antibacterial agent for the specific bacterium. However, a potentiator is not an antibacterial agent when used by itself, therefore a possible potentiator is also evaluated for intrinsic antibacterial activity. To be classed as a potentiator, the test compound should show little or no antibacterial activity when the bacterium is grown in the presence of the test compound (at the concentrations used in the combination test) but the absence of the antibacterial agent.

Thus, identification of a potentiator preferably involves the following general steps, a–f:

(a) growing bacteria resistant to an antibacterial agent in appropriate media in the presence of a combination of the test compound whose potentiator activity is to be determined and a concentration of the antibacterial agent which is below the MIC for the resistant strain but above the MIC for an isogeneic susceptible strain, preferably a concentration which would be obtained after several two-fold serial dilutions of the MIC of the resistant strain, but which is at least two times higher than the MIC for the susceptible strain (if no isogenic susceptible strain is available, the concentration of the antibacterial agent is preferably at least twice the MIC of genetically-related bacteria against which the antibacterial agent is therapeutically effective. Alternatively, the concentration may be set at $2^{-3}$ times the MIC of the resistant strain), and (b) measuring bacterial growth, preferably by a measurement of turbidity. In this initial screen, inhibition of the growth of the resistant bacteria at a concentration of antibacterial agent lower than the MIC of the resistant strain could result from either the potentiating activity of the test compound, or from intrinsic antibacterial activity of the test compound.

In order to determine which activity the compound is exhibiting, compounds which stop bacterial growth in this initial screen are next screened again as above, but in the absence of antibacterial agent. This is carried out by (c) growing the resistant bacteria in appropriate media in the presence of the test compound but in the absence of the antibacterial agent, and (d) measuring the bacterial growth. Compounds which stop bacterial growth in the absence of an antibacterial agent possess intrinsic antibacterial activity. Compounds which do not stop bacterial growth in the absence of an antibacterial agent possess potentiator activity.

Next, the MICs for the antibacterial agent in the presence of the test compounds possessing potentiator activity are measured by (e) growing resistant bacteria in appropriate media in the presence of a combination of the test compound and a range of concentrations of the antibacterial agent, which are obtained from serial two-fold dilutions of the antibacterial agent, where the concentration of the antibacterial agent ranges preferably from at least twice the minimal inhibitory concentration (MIC) for the resistant strain to at least one-half the susceptibility breakpoint for the corresponding susceptible strain, and (f) measuring the bacterial growth in the presence of the combinations of different concentrations of the antibacterial agent and test compound to determine the MIC of the antibacterial agent in the presence of the test compound. Potentiators preferably decrease the MIC of the antibacterial agent to less than or equal to two times the MIC of the susceptible strain.

In a another aspect, this invention provides a method for treating a bacterial infection in a mammal, in particular in a human, specifically including, but not limited to, infections which arise from bacteria which are resistant to one or more antibacterial agents, and where the treatment includes administering a therapeutically or pharmacologically effective amount of a combination of an antibacterial agent with a potentiator.

In a related aspect this invention also provides a method for prophylactic treatment of a mammal, in particular a human, in order to prevent a bacterial infection. Such treatment comprises administering a potentiator and an antibacterial agent to the mammal. Preferably such treatment would be used when the patient is at risk of contracting or developing a bacterial infection.

In addition, in another aspect this invention provides pharmaceutical compositions effective for treatment of a bacterial infection in a mammal, when such a composition is administered in conjunction with an antibacterial agent. Such compositions include at least one suitable carrier and a potentiator compound, and are to be used in combination with a potentiated antibacterial agent for the treatment of an infection in a mammal arising from bacteria resistant to the antibacterial agent. Thus, such a pharmaceutical composition is preferably a mixture of compounds containing the potentiator compound, in a therapeutically effective amount, and a carrier or excipient.

Furthermore, in a related aspect, this invention provides pharmaceutical compositions which contain both a potentiator and a potentiated antibacterial agent, either with or without one or more suitable carriers. The antibacterial agent and the potentiator are present in such amounts that their combination constitutes a therapeutically effective amount.

In a further related aspect this invention provides an antibacterial formulation. Such formulations comprise a potentiator, an antibacterial agent, and a carrier. Thus, these formulations can be used to inhibit the growth of bacteria which are susceptible to a combination of potentiator and antibacterial agent.

In preferred embodiments of the above aspects, the potentiated antibacterial agent is a β-lactam, β-lactam mimic, glycopeptide, macrolide, quinolone, tetracycline, or aminoglycoside. In particular embodiments in which the antibacterial agent is a β-lactam, the agent may be, e.g., ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, imipenem, meropenem, mezlocillin, loracarbef, fluoxacillin, dicloxacillin, cefmenoxime, cefotiam, cefotetan, or biapenem.

In preferred embodiments this invention provides screening methods, treatment methods, pharmaceutical compositions and antibacterial formulations as in the above aspects which contain potentiators which have structures which include a hydroxyl group and a lipophilic carbocyclic structure. Such compounds can be cyclic terpenes and steroids, but can also be members of other structural classes. In particular embodiments, the carbocyclic structure of such potentiators comprises a structure of two or more fused 5 or 6-member rings, preferably two to five rings. Two adjacent rings are preferably 6-member rings. Descriptions of particular embodiments are provided in the Description of the Preferred Embodiments.

The term "susceptible bacterium" or "susceptible strain" is used in describing the effect of a potentiator. This term means that the MIC of such a bacterium for a specific antibacterial agent is not higher than the upper limit of the clinically-acceptable therapeutic concentration range for that agent. If the antibacterial agent is one for which a generally accepted therapeutic concentration range is not known, then the upper limit for the MIC could be taken to be the upper limit of the therapeutic range of structurally comparable antibacterial agents. If neither of the above are appropriate, then, for a bacterium to be designated as susceptible, the MIC of a specific antibacterial agent for a bacterium should be within a range which is practically obtainable in a human or other appropriate mammal without therapeutically unacceptable side effects.

In references to the effect on a bacterium of a test compound or an identified potentiator, the phrases "inducing a susceptible phenotype" and "increasing the susceptibility of a bacterium" refer to reducing the minimal inhibitory concentration (MIC) for a resistant bacterial strain for an antibacterial agent to a concentration preferably less than two times the MIC for the corresponding susceptible strain, or, if the MIC for a corresponding susceptible strain is not available, less than the concentration obtained after several serial two-fold dilutions of the MIC of the resistant strain (preferably at least three). However, the reduction in MIC is not primarily due to an anti-β-lactamase activity, such as inhibiting the β-lactamase present in a bacterium or decreasing the amount of β-lactamase present in a cell. While a potentiator may induce a susceptible phenotype by causing a decrease in the MIC of the resistant strain to preferably within two times the MIC for the corresponding susceptible bacterial strain, the decrease may be to the level of the MIC of the corresponding susceptible strain, or even lower. The term "MIC" refers to the lowest drug concentration that completely inhibits bacterial growth in vitro. The term "susceptibility breakpoint" is the MIC for a strain of bacteria which is susceptible to the antibacterial agent being tested, as defined by the National Committee for Clinical Laboratory Standards (NCCLS) for each antibiotic used alone against the susceptible strain of the species of bacteria.

A "β-lactam mimic" is a compound which does not contain the core β-lactam ring structure, but which "mimics" the antibacterial action of β-lactams. Thus, such a compound, like β-lactams, binds to one or more PBPs, thereby inhibiting the enzymatic activity of those PBPs. Therefore, since β-lactam mimics exert an antibacterial activity in substantially the same manner as β-lactam antibacterial agents, the claims for this invention which include the use of a β-lactam agent should be understood to include the use of a β-lactam mimic.

A "potentiator" or "potentiating compound" refers to a compound which has a synergistic effect on antibacterial activity when used with an antibacterial agent. Thus, a potentiator enhances the antibacterial effect of an antibacterial agent when the two compounds are used in combination, but does not have significant antibacterial activity when used alone at concentrations similar to its concentration in the combination use. For evaluating the intrinsic antibacterial activity of a possible potentiator, the reduction in growth of a bacterium in the presence of a possible potentiator is determined in comparison to the growth of the bacterium in the absence of the possible potentiator. Preferably the reduction in growth of a bacterium will be no more than 25% at concentrations expected to be clinically achievable. If the reduction in growth is 25% or less, then the possible potentiator is designated as having little intrinsic antibacterial activity. In addition, enhancement of the activity of an antibacterial agent by a potentiator is not primarily due to an anti-β-lactamase activity.

As used herein, a "potentiated antibacterial agent" is an antibacterial agent whose antibacterial activity is enhanced by the potentiator being administered.

The term "method of screening" means that the method is suitable, and is typically used, for testing for a particular property or effect in a large number of compounds. Therefore, the method requires only a small amount of time for each compound tested; typically more than one compound is tested simultaneously (as in a 96-well microtiter plate), and preferably significant portions of the procedure can be automated.

"Intrinsic antibacterial activity" refers to the effect of a compound on inhibiting the growth of a bacterium in an appropriate medium with no other antibacterial agent present. As described above, this activity can be determined by comparing the growth of the bacterium in the presence and absence of the test compound in a growth medium which is otherwise the same. As previously indicated, this reduction in growth due to intrinsic antibacterial activity should be no more than 25% for a potentiator at concentrations expected to be clinically achievable, but can be due to either bacteriostatic or bacteriocidal activity.

Use of the term "appropriate medium" or "appropriate growth medium" for growth of a bacterium is the usage generally accepted in the art. Growth of the bacterium in a given medium is therefore sufficiently consistent for experimental purposes, and the medium thus provides at least the factors needed for growth of a culture of that bacterium.

As previously noted, bacterial resistance to some lactams may be due to the presence of a β-lactamase, and therefore such a resistant bacterium could be rendered susceptible by interfering with the presence or activity of the β-lactamase (e.g., inhibiting production of the β-lactamase or inhibiting the enzymatic activity of the β-lactamase). However, the potentiators of this invention do not primarily enhance the activity of an antibacterial agent by any such effect(s) on a β-lactamase, i.e. they do not primarily function as "anti-β-lactamases" in inducing susceptibility to an antibacterial agent. In addition, for potentiators of antibacterial agents which are not substrates of β-lactamases, the presence or absence of effect of the potentiator on a β-lactamase is of no consequence. For potentiators of an antibacterial agent which is a substrate of a β-lactamase, a direct reduction in the amount or activity of a β-lactamase in a bacterium by the potentiator is not the principal mode of enhancing the activity of the antibacterial agent. The magnitude of the potentiator activity (the enhancement of the antibacterial agent) in such a case can be determined by determining the level of potentiator activity in an isogenic bacterial strain which does not produce the active β-lactamase. This activity should be greater than the enhancement of the activity of the antibacterial agent due to inhibition of the β-lactamase.

As used herein, the term "treating" refers to administering a pharmaceutical composition for prophylactic and/or therapeutic purposes. The term "prophylactic treatment" refers to treating a patient who is not yet infected, but who is susceptible to, or otherwise at risk, of a particular infection. The term "therapeutic treatment" refers to administering treatment to a patient already suffering from an infection. Thus, in preferred embodiments, treating is the administration to a mammal (either for therapeutic or prophylactic purposes) of therapeutically effective amounts of a potentiator and an antibacterial agent in combination (either simultaneously or serially).

The term "bacterial infection" refers to the invasion of the host mammal by pathogenic bacteria, specifically including an invasion by bacteria resistant to one or more antibacterial agents (e.g., bacteria resistant to penicillins). This includes the excessive growth of bacteria which are normally present in or on the body of a mammal. More generally, a bacterial infection can be any situation in which the presence of a bacterial population(s) is damaging to a host mammal. Thus, a mammal is "suffering" from a bacterial infection when excessive numbers of a bacterial population are present in or on a mammal's body, or when the effects of the presence of a bacterial population(s) is damaging the cells or other tissue of a mammal.

The term "antibacterial agent" refers to both naturally occurring antibiotics produced by microorganisms to suppress the growth of other microorganisms, and agents synthesized or modified in the laboratory which have either bactericidal or bacteriostatic activity, e.g.,β-lactam antibacterial agents including , e.g., ampicillin, cloxacillin, oxacillin, and piperacillin, cephalosporins and other cephems including, e.g., cefaclor, cefamandole, cefazolin, cefoperazone, cefotaxime, cefoxitin, ceftazidime, ceftriaxone, and cephalothin; carbapenems including, e.g., imipenem and meropenem; and glycopeptides, macrolides, quinolones, tetracyclines, and aminoglycosides. In general, if an antibacterial agent is bacteriostatic, it means that the agent essentially stops bacterial cell growth (but does not kill the bacteria); if the agent is bacteriocidal, it means that the agent kills the bacterial cells (and may stop growth before killing the bacteria).

The term "β-lactam resistant bacteria" refers to bacteria against which a β-lactam antibacterial agent has a minimum inhibitory concentration (MIC) greater than clinically achievable levels of the β-lactam. Clinically achievable levels means drug concentrations reached or maintained in the mammal for a sufficient period to bring about a clinical cure or improvement. More generally, a bacterium resistant to an antibacterial agent has a MIC greater than about 30 times the MIC of an isogeneic susceptible strain.

The term "administration" refers to a method of giving a dosage of an antibacterial pharmaceutical composition to a mammal, where the method is, e.g., topical, oral, intravenous, transdermal, intraperitoneal, or intramuscular. The preferred method of administration can vary depending on various factors, e.g., the components of the pharmaceutical composition, the site of the potential or actual bacterial infection, the bacterium involved, and the severity of an actual bacterial infection.

By "therapeutically effective amount" or "pharmaceutically effective amount" is meant combinations of amounts of a potentiator and an antibacterial agent, as disclosed for this invention, which have a "therapeutic effect", which generally refers to the inhibition, to some extent, of the normal metabolism of bacterial cells causing or contributing to a bacterial infection. The doses of potentiator and antibacterial agent which are useful in combination as a treatment are "therapeutically effective" amounts. Thus, as used herein, a "therapeutically effective amount" means those amounts of potentiator and antibacterial agent, which, when used in combination produce the desired therapeutic effect as judged by clinical trial results and/or model animal infection studies. In particular embodiments, the potentiator and antibacterial agent are combined in predetermined proportions, and thus the "therapeutically effective amount" would be an amount of the combination. This amount, and the amounts of the potentiator and antibacterial agent individually, can be routinely determined by one skilled in the art and will vary depending upon several factors such as the particular bacterial strain involved, and the particular potentiator and antibacterial agent used. This amount can further depend on the patient's height, weight, sex, age, and medical history.

A "therapeutic effect" relieves, to some extent, one or more of the symptoms of the infection, and includes curing an infection. Curing means that the symptoms of active infection are eliminated, including the elimination of excessive numbers of viable bacteria of those involved in the infection. However, certain long-term or permanent effects of the infection may exist even after a cure is obtained (such as extensive tissue damage).

The terms "terpenes" and "steroids" as used herein have their usual chemical definitions. Those definitions refer to the general structure of compounds included in these classes. Those definitions are given in numerous chemical texts, including e.g., Fessenden and Fessenden, *Organic Chemistry*, Morrison and Boyd, *Organic Chemistry*, 4th ed., and Ege, *Organic Chemistry*. Thus, the term "terpene" is a generic term which refers to compounds containing carbon and hydrogen, optionally substituted with nitrogen, oxygen, or sulfur. These compounds typically can be regarded as being built up from isoprene units, and generally contain between 10 and 35 carbon atoms. Terpenes are further classed according to the number of carbon atoms in each molecule, thus monoterpenes contain 10 carbons, sesquiterpenes 15 carbons, diterpenes 20 carbons, sesquiditerpenes 25 carbons, and so on. In particular, cyclic terpenes are those which contain one or more covalently joined ring structures, and steroids contain a tetracyclic structure (general steroid ring structure) comprising three 6-member rings and one 5-member ring. (See also T. L. Ho, *Carbocycle Construction in Terpene Synthesis*, 1988; Blickenstaff et al., Total Synthesis of Steroids, *Organic Chemistry*, Vol. 30, 1974.)

Likewise, "lipophilic" has its usual biochemical meaning. A lipophilic molecule or portion of a molecule thus has low polarity, and so is hydrophobic. As a consequence, a lipophilic molecule can more readily dissolve in non-polar organic solvents than in polar solvents like water, and therefore readily associate with the fatty and fatty acid portions of many cellular lipids.

The usual chemical meaning is also applicable to "carbocyclic". The term indicates that the structure of a compound contains one or more covalently closed ring structures, and that the atoms forming the backbone of the ring are all carbon atoms. The term thus distinguishes carbocyclic from heterocyclic rings in which the ring backbone contains at least one atom which is different from carbon.

The term "mammal" refers to any organism of the Class Mammalia of higher vertebrates that nourish their young with milk secreted by mammary glands, e.g., mouse, rat, and, in particular, human, dog, and cat.

As used herein, the term "$PD_{50}$" refers to the 50% protective dose and is the same as the 50% effective dose ($ED_{50}$) and the 50% curative dose ($CD_{50}$), and is the dose at which 50% of the subjects respond.

The term "pharmacokinetic" refers to drug concentrations present in body fluids and tissues after administering the drug, and factors that influence how concentrations of the drug vary over time.

The term "pharmacodynamic" refers to the effects of drugs on the body and the biochemical and physiological mechanism of the action of the drugs.

Other features and advantages of the invention will be apparent from the following description of the preferred embodiments, and from the claims.

Figure 1A:
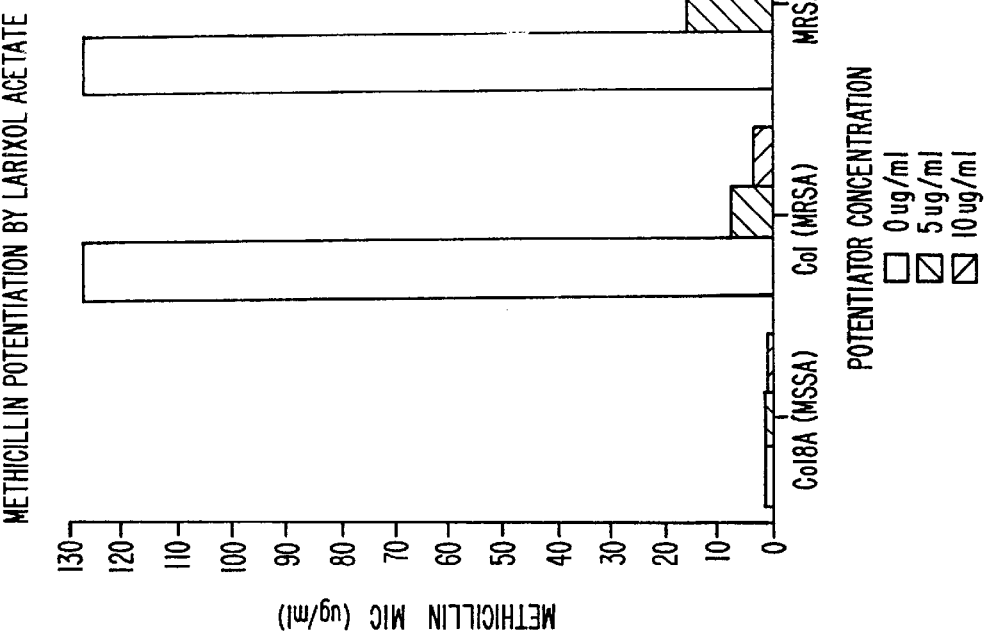
FIG. 1 presents bar graphs showing the potentiation effect of two small molecules, 2-hydroxy-8-methoxy-4a-methyl-1,2,3,4,4a,4b,5,6,10b,11,12,12a-dodecahydrochrysene (HMM-dodecahydrochrysene) and larixol acetate, in reducing the methicillin MIC for two MRSA strains (Col and MRSA76) in comparison with the absence of a reduction in the MIC of a methicillin sensitive strain (Col8A). The methicillin MIC at 0, 5, and 10 μg/ml of the potentiating molecules is shown. The structures of the two potentiating molecules are also shown. These potentiators were identified by screening by the methods of Examples 1 and 2, and the MIC reduction evaluated by the method of Example 3.
Figure 1B:
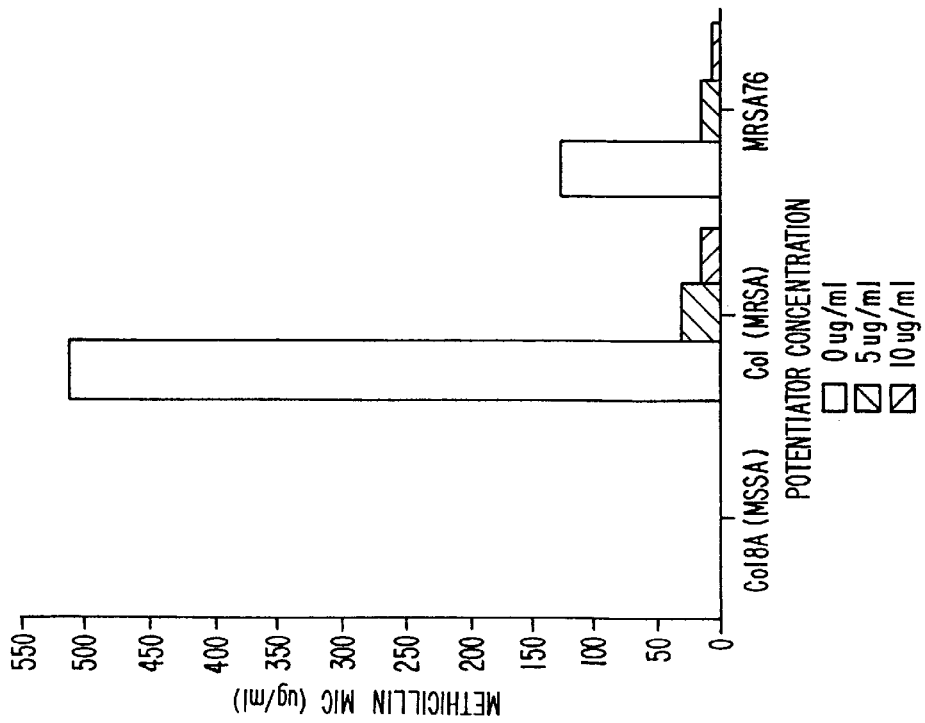
Figure 3A:
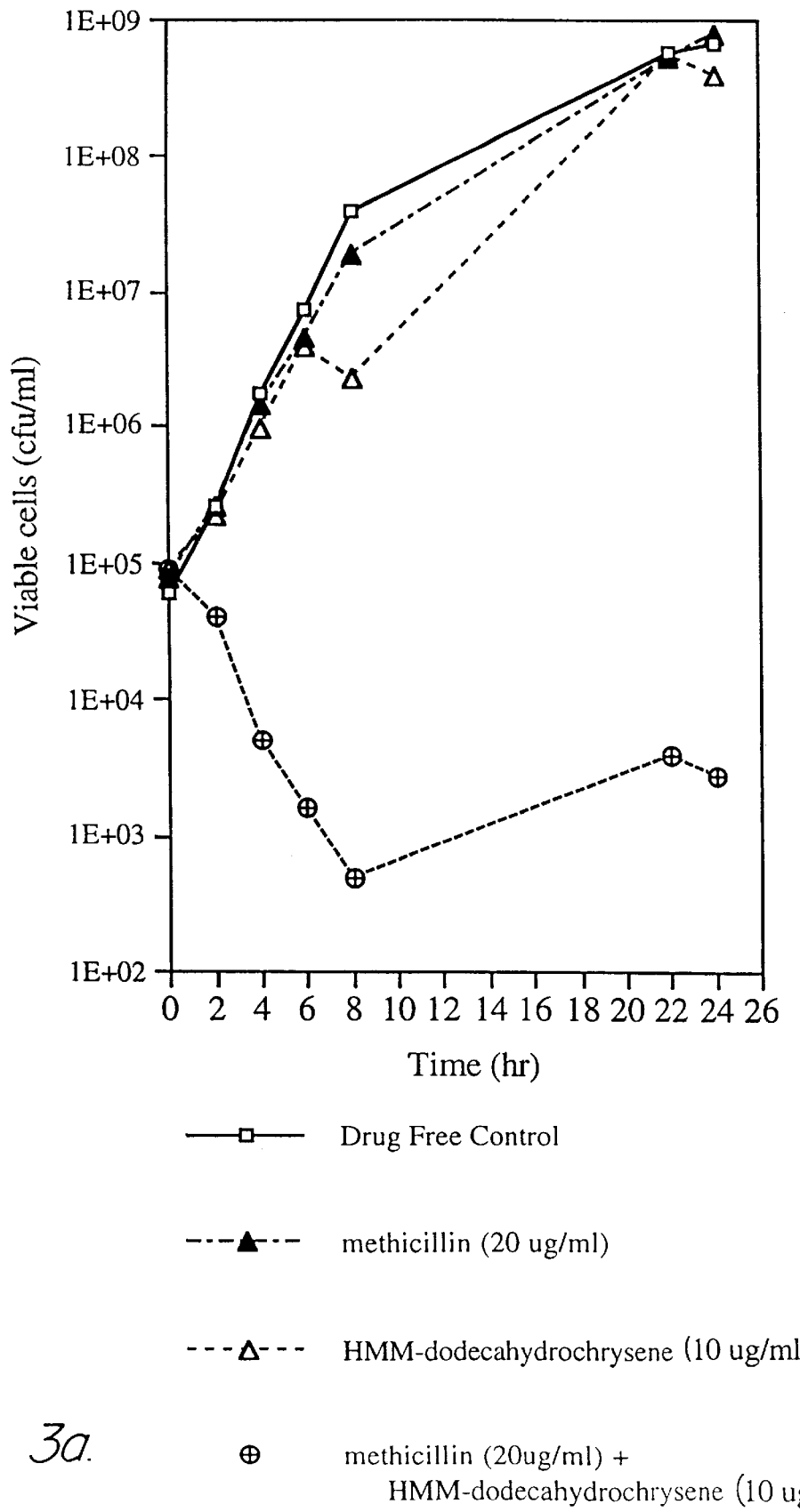
FIG. 3a is a graph of the number of viable MRSA Col cells/ml versus growth time in hours as determined by the method of Example 4. The graph presents the time kill curve for the first potentiating compound from FIG. 1 at 10 μg/ml with methicillin at 20 μg/ml, and curves for controls (drug-free, methicillin only, and potentiator only). Viable cell counts for all controls were greater than $5\times10^8$ cells/ml at 24 hours, while the viable cell count for methicillin plus potentiator was approximately $5\times10^3$ cells/ml after 24 hours.
Figure 3B:
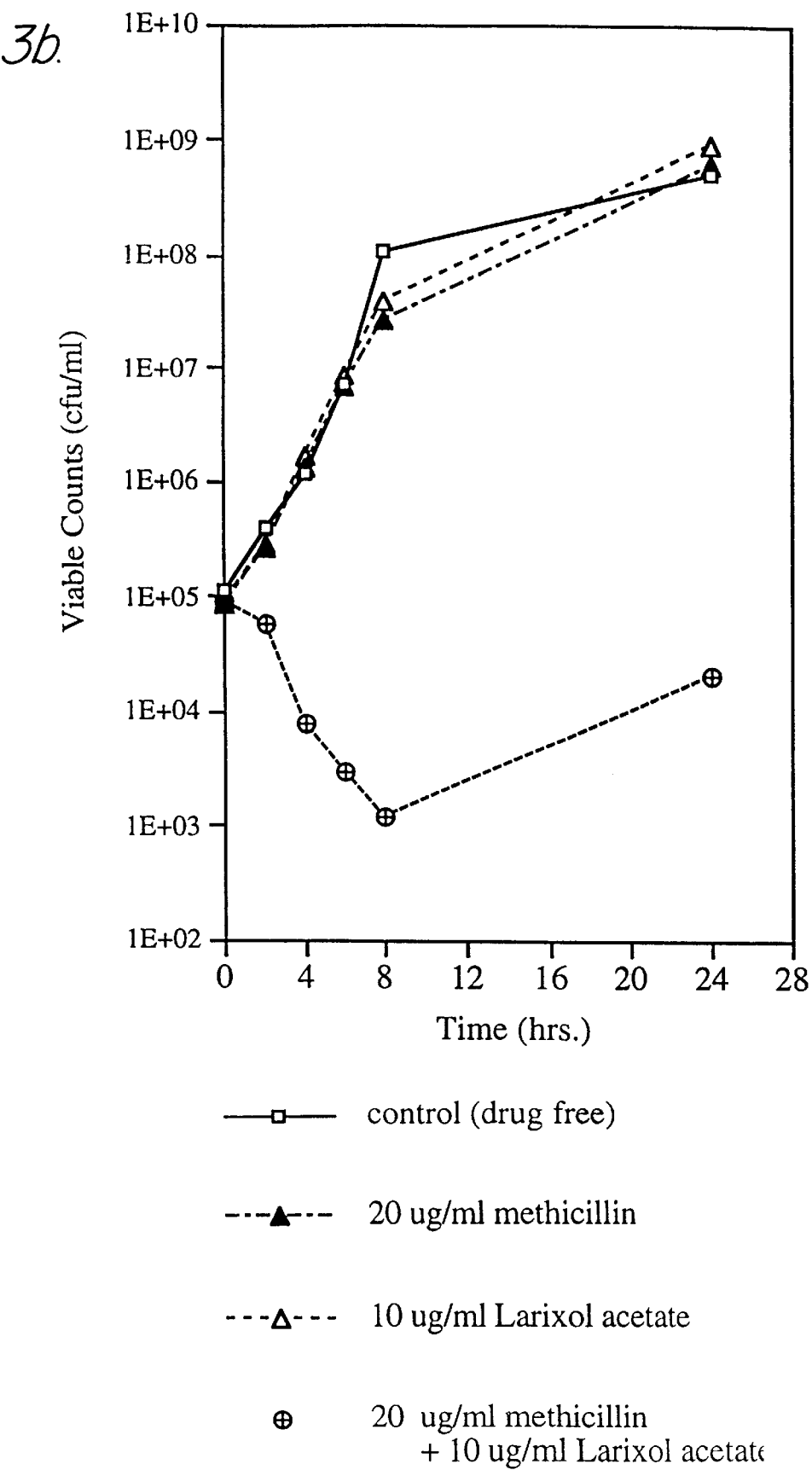

Similar to FIG. 3a, FIG. 3b is a graph of the number of viable MRSA Col cells/ml versus growth time in hours. The graph shows the time kill curve for the second potentiating compound from FIG. 1 with methicillin, and curves for controls.

Figures 2, 9B:
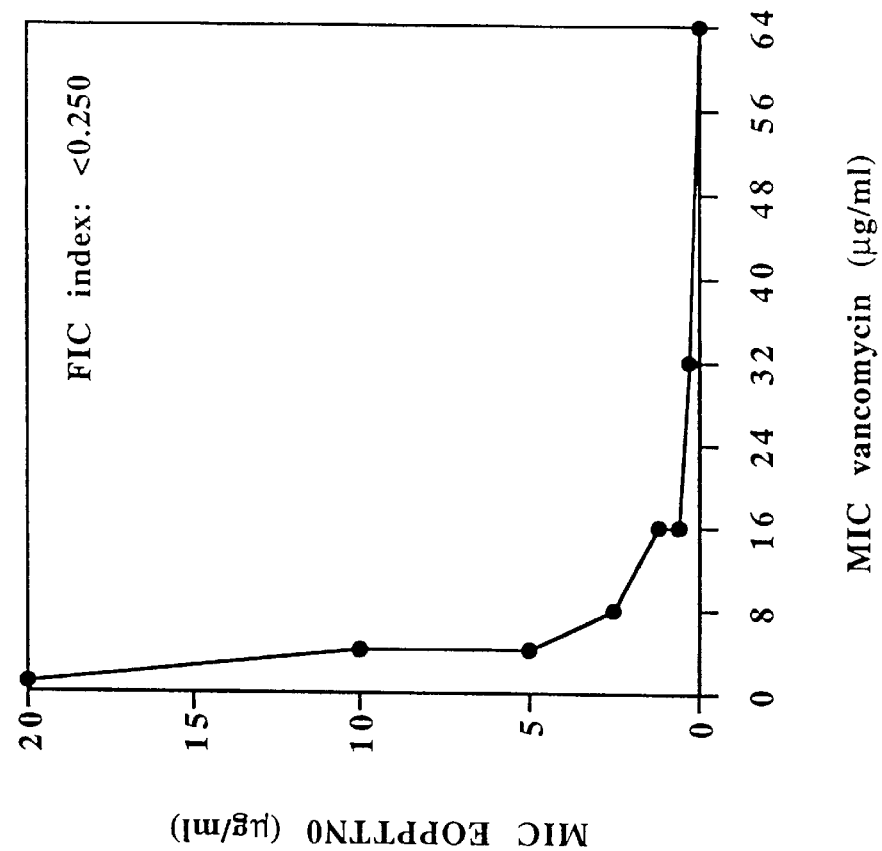
FIG. 2 is a table showing the potentiating effect of one of the potentiating molecules from FIG. 1 for 17 antimicrobial agents in MRSA strain Col. The MIC is shown at 0, 5, and 10 μg/ml of potentiator. Significant MIC reduction occurred for a range of β-lactams, including methicillin, cefazolin, and imipenem, among others.
Figures 1, 9B:
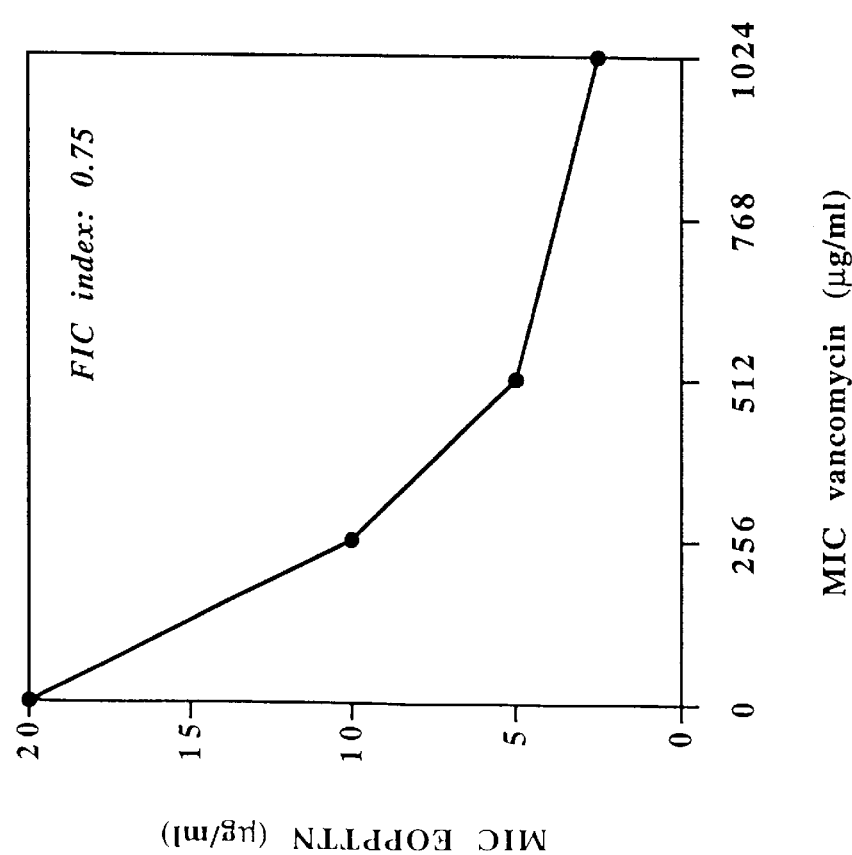

FIG. 4 is a table showing the imipenem potentiation effect of the second compound from FIG. 1 at 10 μg/ml in 5 MRSA strains (Col, Col 2278, sa 038, Spain 356, and Spain 195). The MIC was reduced by three orders of magnitude in strains Col, Col 2278, and Spain 195.

FIG. 5a and 5b are tables showing the methicillin potentiation effect of one of the molecules shown in FIG. 1 in comparison with various analogs of that molecule. For each analog, MICs are shown for 0, 5, and 10 μg/ml of that compound with two MRSA strains (Col and Strain 76) and one methicillin susceptible strain (Col8A). FIG. 5c is a table showing the methicillin potentiation effect of the other molecule from FIG. 1 in comparison with various analogs of that molecule. MICs are shown as for FIGS. 5a and 5b.

FIGS. 6a–6f show the structures of the compounds listed in FIGS. 5a–5c, along with the MIC for methicillin with the test compound at 5 μg/ml.

Figure 7:
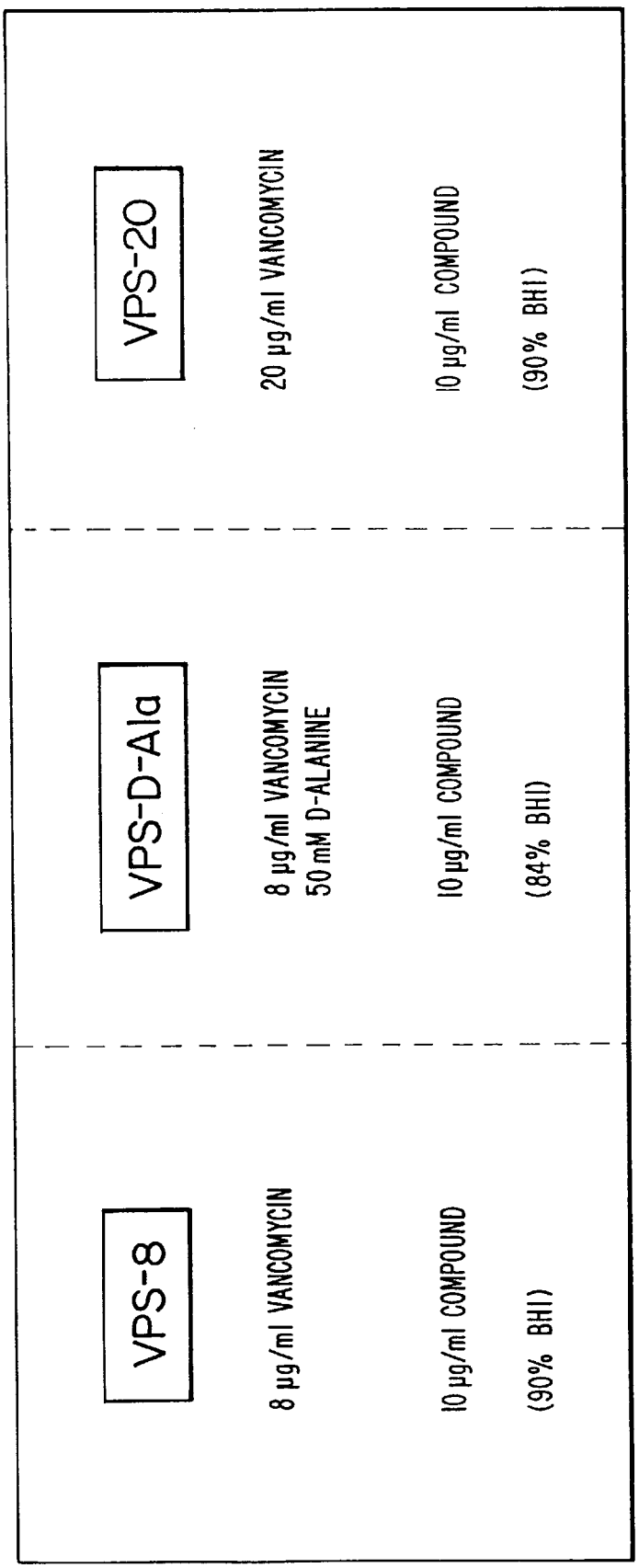

FIG. 7 lists three glycopeptide potentiation screening assays using vancomycin, and shows the differences between the assays in vancomycin concentration and presence of D-alanine supplement.

FIG. 8 shows the structures of three compounds which were preliminary hits in the VPS-20 and VPS-D-ala assays, N-benzyl thiosalicylamide, brazilin, and 6-ethyl-7-[1-oxo-3-(1-pyrrolidino)]propyl-1,2,3,4-tetrahydor-1,1,4,4-tetramethylnaphthalene (EOPPTTN). The figure also provides the percent bacterial growth inhibition observed in the VPS-20 and VPS-D-ala assays for each of the three preliminary hits shown, along with the growth inhibition observed for the compound in the absence of vancomycin (intrinsic inhibition). For each pair of numbers, the first number indicates the observed growth inhibition percentage in the presence of vancomycin, while the second number indicates the percent intrinsic inhibition. For example, for 88/4, there was 88% growth inhibition for the test compound with vancomycin, and only 4% intrinsic inhibition.

FIG. 9a provides the results of checkerboard assays showing the MIC reduction for vancomycin in the presence of a range of concentrations of brazilin against two *Enterococcus faecalis* strains, one VanA and the other VanB. Both strains show a significant reduction in the vancomycin MIC over a range of brazilin concentrations from 0–20 μg/ml. Similarly, FIG. 9b provides the results of checkerboard assays showing the MIC reduction for vancomycin in the presence of a range of concentrations of 6-ethyl-7-[1-oxo-3-(1-pyrrolidino)]propyl-1,2,3,4-tetrahydro-1,1,4,4-tetramethylnaphthalene (EOPPTTN). Similar to the results in FIG. 9a, the vancomycin MIC declined significantly as the concentration of EOPPTTN was increased from 0 to 20 μg/ml.

DESCRIPTION OF THE PREFERRED EMBODIMENTS

Potentiation Screening Assays

The present invention features a method for screening for compounds which potentiate the effects of antibacterial agents on bacterial cell growth. The potentiation screening assay is a test for determining whether test compounds enhance the ability of an antibacterial agent to stop bacterial growth. Briefly, the potentiation screening assay is a high-throughput whole cell assay in which compounds of unknown pharmacological activity are tested for their ability to induce an antibacterial-agent-susceptible phenotype. The term "high-throughput" refers to the capacity to test large numbers of compounds efficiently, typically implying that a number of compounds are tested simultaneously. For example, using 96-well microtiter plates, up to 96 compounds can be tested at a time. In addition, the capacity can be increased by using more than one 96 well plate.

In a preferred embodiment, the potentiation screen can be used to detect potentiators of methicillin and other β-lactam antibacterial agents. In that embodiment, MRSA are grown in the presence of methicillin and various test compounds. The concentration of methicillin used is preferably the concentration obtained after several serial two-fold dilutions of the MIC for the MRSA strain, so that the methicillin alone will not kill the cells. This level of methicillin, however, is preferably at least twice the MIC for most methicillin susceptible *S. aureus* (MSSA), and should therefore repress growth or kill cells in cases where the MSSA phenotype has appeared. Growth is assessed after 5–24 hours by turbidity. The appropriate growth period prior to reading turbidity will depend on the growth rate of the bacterium used in this potentiator screen, or in similar screens using other bacterial species. (Note that testing for potentiators using MRSA is essentially the same if MRSE is used, since the same mechanism of resistance is present in both groups. Thus, the description, herein of embodiments using susceptible or resistant *Staphylococcus aureus* in methods of testing for potentiators, or methods of using potentiators, should be understood to include similar susceptible or resistant *Staphylococcus epidermidis*, even if not specifically so indicated.)

In order to determine whether the antibacterial effects observed in the potentiation screen have resulted from potentiator activity or from intrinsic antibacterial activity of the test compound, the compounds are also screened for intrinsic antibacterial activity in the assay described above, except in the absence of the antibacterial agent. Compounds which show no, or only slight, intrinsic activity but which repress growth when used together with the antibacterial agent are considered potentiators of β-lactam agents. The MICs for β-lactam agents in the presence of the β-lactam potentiators can then be determined by growing the MRSA in appropriate media in the presence of a combination of the β-lactam potentiator, and a range of concentrations of the β-lactam agent, which are obtained from serial two-fold dilutions of the β-lactam agent, where the concentration of the antibacterial agent ranges preferably from at least twice the minimal inhibitory concentration (MIC) for the MRSA to at least one-half the MIC for the MSSA. Measurements of the bacterial growth in the presence of the combinations of different concentrations of the β-lactam agent and β-lactam potentiator can be used to determine the MIC of the β-lactam agent in the presence of the β-lactam potentiator. In one preferred embodiment, the MIC for the β-lactam agent is measured in the presence of 0 μg/ml, 5μg/ml, and 10 μg/ml of the potentiator.

In another preferred embodiment the potentiation screen can be used to detect potentiators of ampicillin in *Enterococcus faecium*. In a manner similar to the methicillin potentiation screen in MRSA, highly ampicillin resistant *E. faecium* are grown in the presence of a combination of ampicillin and various concentrations of a test compound. The ampicillin is at a concentration well below the MIC for the resistant strain of bacteria, but above the MIC for the isogenic resistant strain. Growth is evaluated after 5–24 hours by measuring turbidity. Compounds which show activity in the first test are also evaluated for intrinsic antibacterial activity, by growing the bacteria in the absence of ampicillin but in the presence of the test compound. Those compounds which enhance the antibacterial activity of ampicillin, but which show no, or only a little, intrinsic antibacterial activity are considered potentiators.

Likewise, in other preferred embodiments, other bacterial strains and species resistant to one or more antibacterial agents are used and/or compounds are tested for their ability to potentiate the activity of other antibacterial agents, e.g., a glycopeptide.

Compounds to be screened and preferred potentiators

The screening method of the present invention is appropriate and useful for testing compounds from a variety of sources for possible potentiator activity. The initial screens were performed using a diverse library of compounds, but is suitable for a variety of other compound libraries. Such compound libraries can be combinatorial libraries, natural product libraries, or other small molecule libraries. In addition, compounds from commercial sources can be tested; this testing is particularly appropriate for commercially available analogs of identified potentiators.

Certain of the compounds identified as potentiators of methicillin have a general structure consisting of a hydroxyl group attached to an optionally substituted lipophilic carbocyclic framework. (See structures of HMM-dodecahydrochrysene and larixol acetate, FIG. 1, bottom.) Therefore, compound libraries containing such compounds are particularly appropriate to test. Compounds of the above general structure can be found in the cyclic terpene and steroid classes of structures, but are not limited to those classes.

In particular embodiments, potentiators are compounds which are structurally related to the identified potentiators, HMM-dodecahydrochrysene and larixol acetate, and their pharmaceutically acceptable salts. Such related compounds can be represented by a general structure, Structure 1 below:

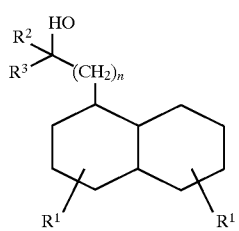

Structure 1 wherein $R^1$ and $R^2$ are selected from the group consisting of H, alkyl, and alkenyl, and either $R^1$ or $R^2$ may be methylene or methine attached to ring B to form another ring, A.

$R^3$ and $R^4$ are selected from the group consisting of H, alkyl, halogen, alkoxy, acyloxy, oxo, or together may be joined to form a 5 or 6-membered ring, D. Ring D may have fused to it a 5 or 6-membered ring E.

$R^5$ is selected from H or alkyl, but is preferably H.

Rings A, B, C, D, and E may be aliphatic or aromatic; where they are aliphatic, the individual bonds in these rings may be single or double bonds. The ring junctures may be either cis or trans. These rings may be optionally substituted by one or more groups selected from alkyl, halogen, acyloxy, alkoxy, or oxo.

The structures of compounds having Structure 1 are more easily seen by considering two different general structures, Structures 2 & 3, as embodiments of Structure 1 compounds:

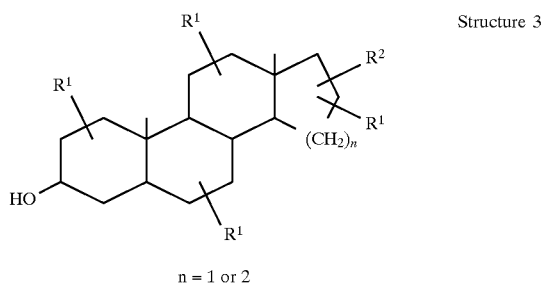

Structure 2 n = 1–4

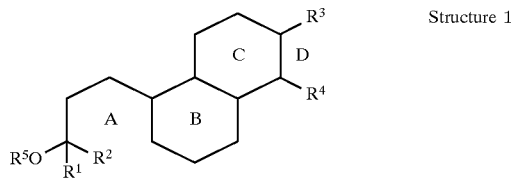

Structure 3 n = 1 or 2

In some preferred embodiments, the potentiators have Structure 2. As in Structure 1, the rings may be aliphatic, aromatic, or may contain 1 or 2 carbon-carbon double bonds.

The ring structure can be optionally substituted with one or more substituents, $R^1$, wherein $R^1$ is alkyl, alkoxy, acetyloxy, or halogen, but preferably alkyl, and more preferably methyl. Preferably no more than one substituent, $R^1$, is alkoxy or acetyloxy. $R^2$ and $R^3$ are independently H, alkyl, or alkenyl, or either may form another 5 or 6-member ring.

In another embodiment the potentiators have Structure 3. Similarly to Structure 2 potentiators, the rings may be aliphatic, aromatic or may contain 1 or 2 carbon-carbon double bonds. The ring structure can be optionally substituted with one or more substituents, $R^1$, wherein $R^1$ is alkyl, alkoxy, or acetyloxy, but preferably alkyl, and more preferably methyl. Preferably no more than one substituent, $R^1$, is alkoxy or acetyloxy. $R^2$ is H, alkyl, alkenyl, alkoxy, acyloxy, or hydroxyalkyl, but preferably only one substituent, $R^1$ or $R^2$, is alkoxy, acyloxy, or hydroxyalkyl.

As used herein, the term "alkyl" refers to an aliphatic hydrocarbon, preferably a saturated hydrocarbon, either unbranched or branched. Preferably the alkyl group contains one to six carbons, more preferably from one to four carbons, such as, e.g., methyl, ethyl, n-propyl, iso-propyl, n-butyl, sec-butyl, iso-butyl and tert-butyl. The alkyl group may be optionally substituted with one or more functional groups which are attached commonly to such chains, preferably hydroxyl, bromo, fluoro, chloro, iodo, mercapto or thio, cyano, alkylthio, heterocycle, aryl, heteroaryl, carboxyl, carboalkoyl, alkyl, alkenyl, nitro, amino, alkoxyl, amido, and the like.

The term "alkenyl" denotes an alkyl group as defined above having at least one double bond, such as, e.g., vinyl, allyl, 1-propenyl, isopropenyl, 1-butenyl, 2-butenyl, 3-butenyl, methallyl, or 1,1-dimethylallyl.

The term "alkoxyl" denotes the group —OR, where R is alkyl as defined above, such as methoxy, ethoxy, n-propoxy, iso-propoxy, n-butoxy, sec-butoxy, iso-butoxy, or tert-butoxy and the like.

The term "acyl" denotes groups -C(O)R, where R is alkyl as defined above, such as formyl, acetyl, propionyl, or butyryl.

The term "acyloxy" denotes groups —OC(O)R, where R is alkyl as defined above, such as acetyloxy.

The term hydroxyalkyl denotes groups —R—OH, where R is alkyl as defined above.

The most preferred embodiments of the potentiator include 2-hydroxy-8-methoxy-4a-methyl-1,2,3,4,4a,4b,5,6,-10b,11,12, 1A-dodecahydrochrysene (dodecahydrochrysene) and larixol acetate, and their analogs including, e.g., 5-α-androstan-3β-ol, 5β-androstan-3-α-ol, 5β-androstan-3β-ol, β-estradiol 3-methyl ether, epiandrosterone acetate, 10a, 12a-dimethyl-1,8-hydroxy-tetradecahydrochrysene, and uvaol.

Synthesis of Structure 1 and other related compounds:

Certain of the compounds which show potentiating activity, or which are appropriate to test can be obtained from commercial sources, such as Aldrich Chemical Co., Inc. (Milwaukee, Wisc.), Sigma Chemical Co. (St. Louis, Mo.), Janssen Parmaceutica (Beerse, Belgium), Lancaster, or Fluka.

However, in general, the synthesis of compounds similar to Structure 1 may be achieved using standard, well-known methods and readily available materials according to methods found in the following monographs: Ho, T. L., *Carbocycle Construction in Terpene Synthesis* (VCH Verlagsgesellschaft, Fed. Rep. Ger., 1988); Blickenstaff, R. T., et al., Organic Chemistry, Vol. 30: *Total Synthesis of Steroids* (Academic, New York, 1974).

Pharmacologic evaluation criteria

It is desirable, but not essential, that the potentiators meet the following pharmacologic criteria:

(1) Potentiation of an antibacterial agent, e.g., methicillin, other β-lactams, or other antimicrobial agents, (2) Little or no inhibition of target organisms, e.g., *S. aureus*, when used alone, (3) Ability to reduce the MIC of antibacterial agents, e.g., β-lactam agents and glycopeptide agents, to preferably less than or equal to two times the MIC of a strain susceptible to that agent, (4) Bactericidal or bacteriostatic activity verifiable by time-kill studies, (5) Toxicity in mice only at concentrations similar to marketed antibacterial agents, (6) When combined with antibacterial agents, e.g., methicillin or other β-lactams (or other antibacterial agents), the potentiator/antibacterial agent combination results in a decrease of the $PD_{50}$ in mice in accordance with anticipated clinical utility (in the 1 mg/kg range), and (7) Pharmacokinetic and pharmacodynamic characteristics comparable to the coadministered antibiotics.

In vitro Applications

Potentiators may be used in vitro together with antibacterial agents in tissue culture media to prevent contamination of eukaryotic cell cultures with antibacterial-agent resistant bacteria. In a preferred embodiment, potentiators of β-lactam agents can be added to tissue culture media together with a β-lactam agent to prevent contamination by MRSA.

Pharmaceutical Applications

The compositions containing potentiators can be administered for prophylactic and/or therapeutic treatments. In therapeutic applications, the compositions are administered to a patient already suffering from an infection from bacteria resistant to an antibacterial agent, in an amount sufficient to cure or at least partially arrest the symptoms of the infection. An amount adequate to accomplish this is defined as "therapeutically effective amount or dose." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to, or otherwise at risk of, a particular infection. Such an amount is defined to be a "prophylactically effective amount or dose." In this use, the precise amounts again depend on the patient's state of health, weight, and the like.

Once improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms.

Administration

Although it is possible to administer the combination of potentiator together with the potentiated antibacterial agent alone, it is preferable to present them as part of a pharmaceutical composition containing the active combination of compounds and a carrier or excipient.

The formulations of the present invention preferably contain at least one potentiating compound together with an antibacterial agent and one or more pharmaceutically or therapeutically acceptable carriers or excipients. The potentiating compound and antibacterial agent are in such amounts and relative proportion that the combination constitutes a pharmaceutically or therapeutically effective dose or amount. The compounds can be prepared as pharmaceutically acceptable salts (i.e., non-toxic salts which do not prevent the compound from exerting its effect).

Carriers or excipient can be used to facilitate administration of the compound, for example, to increase the solubility of the compound. Solid carriers include, e.g., starch, lactose, dicalcium phosphate, microcrystalline cellulose, sucrose, and kaolin, and optionally other therapeutic ingredients. Liquid carriers include, e.g., sterile water, saline, buffers, polyethylene glycols, non-ionic surfactants, and edible oils such as corn, peanut and sesame oils, and other compounds described e.g., in the MERCK INDEX, Merck & Co., Rahway, N.J. In addition, various adjuvants such as are commonly used in the art may be included. For example: flavoring agents, coloring agents, preservatives, and antioxidants, e.g., vitamin E, ascorbic acid, BHT and BHA. Various other considerations are described, e.g., in Gilman et al. (eds) (1990) *Goodman and Gilman's: The Pharmacological Basis of Therapeutics*, 8th Ed., Pergamon Press. Methods for administration are discussed therein, e.g., for oral, intravenous, intraperitoneal, or intramuscular administration, subcutaneous, topically, and others. Generally, preferred routes of administration are intravenous and intramuscular.

These pharmaceutical compositions can be in a variety of forms. These include, for example, solid, semi-solid and liquid dosage forms, such as tablets, pills, powders, liquid solutions or suspensions, liposomes, injectable and infusible solutions. The preferred form depends on the intended mode of administration and therapeutic application. For some compounds a pharmacologically acceptable salt of the compound will be used to simplify preparation of the composition. Preferred salts include sodium, potassium, arginine, glycine, alanine, threonine. These are prepared, preferably, in water suitably mixed with a surfactant such as hydroxypropylcellulose.

EXAMPLES

Examples are provided below to illustrate various aspects and embodiments of the present invention. These examples are not intended in any way to limit the disclosed invention. Rather, they illustrate methodology by which potentiators can be readily identified by routine procedure to ensure that they have the desired potentiator activity. That is, compounds within the formula claimed herein can be tested to determine those with the most activity prior to administration to an animal or human. Other compounds can also be screened to determine suitability for use in methods of this invention.

Example 1

Potentiation Screening Assay; Initial Screen

As a first assessment of whether the compound can potentiate the effect of another antibacterial agent, a whole cell growth inhibition assay is run in the presence of both the test compound and the antibacterial agent, with the antibacterial agent at a concentration of approximately ⅕ the MIC of the antibiotic alone.

When testing for a combination that can be used against MRSA (MIC of methicillin >100 $\mu$g/ml), the MRSA cells are grown in the presence of 5 $\mu$g/ml test compound and 20 $\mu$g/ml methicillin as follows: A fresh inoculum of MRSA cells is grown at 35° C. in Mueller-Hinton Broth (MHB) overnight and then diluted 1/50 in the same medium. After regrowth at 35° C. to an $OD_{600}$ of 0.2–0.4 (1–2 hrs.), the cells are diluted 1/1000 in MHB. In a microtiter plate, 50 $\mu$l of this diluted culture is combined with 50 $\mu$l MHB containing 10 $\mu$g/ml test compound and 40 $\mu$g/ml methicillin to give starting growth conditions of 5×10$^5$ cfu/ml in MHB, with 5 $\mu$g/ml test compound and 20 $\mu$g/ml methicillin. The plate is placed in a humidified 35° C. incubator for 5–24 hours, and cell growth or inhibition is read as turbidity ($OD_{600}$). Two positive and one negative controls for growth are cells grown MHB, cells grown in MHB plus 20 $\mu$g/ml methicillin alone (without test compound), and uninoculated MHB respectively. In order to be carried forward to the next step of the potentiator screening assay, a compound must significantly inhibit growth (equal to or less than 50% of the growth of the positive control with methicillin) in this assay.

Example 2

Potentiation Screening Assay: Specificity

In order to ascertain that the test compound is not primarily responsible for inhibition of growth, MRSA cells are grown in the presence of 5 $\mu$g/ml test compound as follows: A fresh inoculum of MRSA cells is grown at 35° C. in Mueller-Hinton Broth (MHB) overnight and then diluted 1/50 in the same medium. After regrowth at 35° C. to an $OD_{600}$ of 0.2–0.4 (1–2 hrs.), the cells are diluted 1/1000 in MHB. In a microtiter plate, 50 $\mu$l of this diluted culture is combined with 50 $\mu$l MHB containing 10 $\mu$g/ml test compound to give starting growth conditions of 5×10$^5$ cfu/ml in MHB, with 5 $\mu$g/ml test compound. The plate is placed in a humidified 35° C. incubator for 5–24 hours, and cell growth or inhibition is read as turbidity ($OD_{600}$). To be carried forward to the next step of the potentiator screening assay, the test compound should have little or no intrinsic anti-staphylococcal activity (growth should be at least 75% of the growth of the positive control without methicillin, corrected for background), or that activity should be explicable without indicating the probability of human toxicity.

Example 3

Potentiation Screening Assay: MIC Reduction

Compounds which meet the first two criteria for follow-up are evaluated in a standard microdilution assessment of the MIC with methicillin for MRSA. (see Lorian, *Antibiotics in Laboratory Medicine,* 3rd ed., pp. 72–75 (1991).) In order to be carried further, the MIC of methicillin preferably is reduced in the presence of the potentiator to at most twice the MIC of a susceptible strain for methicillin. (However, that level of reduction is not essential, since in particular circumstances a potentiator which provides a lesser reduction in the MIC can be useful.) In cases where susceptibility breakpoints are not available or the organism is not resistant to the drug whose action is being potentiated, the MIC preferably must be reduced by several twofold dilutions. We describe herein two compounds identified as having methicillin potentiating activity. These two potentiators meet the first three desired pharmacologic criteria as described above: (1) Potentiation of an anti-bacterial agent, (2) Little or no inhibition of the target organisms when used alone, and (3) Ability to reduce the MIC of an antibacterial agent to less than or equal to two times the MIC of an equivalent bacterial strain susceptible to that agent. Both compounds reduce the MIC of methicillin to below the susceptibility breakpoint (see FIG. 2 for larixol acetate data).

Compounds which have been tested and found to reduce the MIC for methicillin, while not exhibiting intrinsic antimicrobial activity, include 2-hydroxy-8-methoxy-4a-methyl-1,2,3,4,4a,4b,5,6,10b,11,12,12a-dodecahydrochrysene and larixol acetate and their analogs including, e.g., 5-α-androstan-3β-ol, 5β-androstan-3-α-ol, 5β-androstan-3β-ol, and β-estradiol-3-methyl ether, 10a, 12a dimethyl 1-8-hydroxy-tetradecahydrochrysene, and uvaol. Other analogs were found to have little or no effect on the MIC for methicillin. These ineffective compounds include α-estradiol, β-estradiol, epiandrosterone, ergocalciferol, 6-methoxy-1,2,3,4-tetrahydronaphthalene, 6,7-dimethoxy-1-tetralone, 6-methoxy-1-tetralone, dextromethorphan, methyl o-methyl-podocarpate, (3aR) -(+) -sclareolide, 4a, 5-epoxy-3-oxo-14H-4,6a,9,9-4mephenanthro (2,3-D)(1,3)dioxole-4-propionic acid, and andrographolide. The results obtained from these test compounds and others are shown in FIGS. 5a, 5b, and 5c.

MICs for the compounds were determined in the presence of 0, 5, and 10 $\mu$g/ml of each compound. MRSA cells were grown in the presence of 0, 5, and 10 $\mu$g/ml test compound and concentrations of methicillin obtained from serial two-fold dilutions starting at 1024 $\mu$g/ml to 0.002 $\mu$g/ml (This range can be extended or refined as appropriate.) as follows: A fresh inoculum of MRSA cells was grown at 35° C. in Mueller-Hinton Broth (MHB) overnight and then diluted 1/50 in the same medium. After regrowth at 35° C. to an $OD_{600}$ of 0.2–0.4 (1–2 hrs.), the cells were diluted 1/1000 in MHB. In a microtiter plate, 50 $\mu$l of this diluted culture were combined with 50 $\mu$l MHB containing 0, 10, or 20 $\mu$g/ml test compound to give starting growth conditions of 5×10$^5$cfu/ml in MHB, with 0, 5, or 10 $\mu$g/ml test compound. The plate was placed in a humidified 35° C. incubator for 24 hours, and cell growth or inhibition was read as turbidity ($OD_{600}$).

In a standard checkerboard assay in which the MIC is determined in the absence and presence of two concentrations of test compound, these compounds show Fractional Inhibitory Concentration Indices (FIC indices) less than 0.2 when combined with methicillin, indicating very significant synergism. The FIC is the concentration of an antimicrobial agent needed to obtain a given level of growth inhibition in the presence of the test compound divided by the concentration of the same antimicrobial agent needed to obtain the same level of growth inhibition in the absence of the test compound. (For descriptions of the calculation of FICs and FIC indices see Elion et al., *J. Biol. Chem.* 208:477–488 (1954), and Eliopolous & Moellering, Ch. 13 in *Antibiotics in Laboratory Medicine,* 3rd ed., Lorian ed., at pp. 434–441.)

The compounds also show the ability to potentiate the activity of a variety of β-lactams against several different MRSA strains, and show little or no potentiation of the activity of non-β-lactam drugs against MRSA strains that are susceptible to those drugs in vitro. The data for larixol acetate is shown in FIG. 2.

A variety of structural analogs were tested for their ability to potentiate methicillin, and they show a range of activity that will make it possible to glean a tentative structure-activity relationship (FIGS. 5a,b,c,). An initial study indicates that the compounds do not appear to bind directly to the PBP2a active site, nor do they stimulate PBP2a binding of methicillin itself (data not shown).

Example 4

Time-kill Curves

A standard time-kill method (see Eliopolous & Moellering, Ch. 13 in *Antibiotics in Laboratory Medicine,* 3rd ed., Lorian ed., at pp. 441–444) is used to characterize whether the potentiator-drug combination is bacteriostatic or bactericidal. As controls, normal growth of the pathogen (without drug or potentiator) and the effects of the drug alone and the potentiator alone are assessed using the same inoculum culture as is used in the combination time-kill test. Either bacteriostatic or bactericidal effect should be confirmed for the potentiators to progress to further testing.

Example 5

In vivo modeling: Gross Toxicity

Gross acute toxicity is assessed in a mouse model. The potentiator is administered at a range of doses, including high doses, (typically 0–100 mg/kg, but preferably to at least 100 times the expected therapeutic dose) subcutaneously or orally, as appropriate, to healthy mice. The mice are observed for 3–10 days. In the same way, the combination of potentiator and β-lactam is tested for possible acute toxicity.

Example 6

Pharmaceutical Applications

The potentiators can be used to treat infections arising from bacteria resistant to antibacterial agents. According to this invention, a therapeutically or pharmaceutically effective amount of a potentiator and particularly, a compound of Structure 1, is administered to a mammal suffering from an infection arising from antibacterial agent-resistant bacteria, in an amount effective to at least partially relieve the infection. In one preferred embodiment, a β-lactam agent is administered to a mammal suffering from an infection arising from β-lactam resistant *S. aureus* in an amount effective to at least partially relieve the infection. Especially important are infections resulting from multi-drug resistant strains of *S. aureus, E. faecium,* and *E. faecalis.*

In general, a suitable effective dose of a potentiator of the invention will be in the range of 0.1 to 1000 milligrams (mg) per recipient per day, preferably in the range of 1 to 100 mg per day. The desired dosage is preferably presented in one, two, three, four or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 25 mg/kg of patient body weight, between about one to four times per day.

Example 7

Biological Activity

The potentiator test compounds are evaluated against several β-lactam resistant bacteria strains by determining the minimum inhibitory concentration (MIC, µg/ml) of a β-lactam antibacterial agent in the presence of each potentiator with respect to each strain. The MIC, the lowest concentration of antibacterial agent which inhibits growth of the test organism, is determined by the agar dilution method. To determine the MIC for bacterial isolates, the test compound was incorporated in a series of two-fold dilutions into liquefied Mueller-Hinton II agar. Upon solidification, a number of different bacterial strains are spot inoculated with a replicating device onto the agar surface. After overnight incubation, the MIC is determined as the lowest drug concentration that completely inhibited growth, disregarding a single colony or a faint haze. The procedures used in these studies have been standardized by the National Committee for Clinical Laboratory Standards (NCCLS), as per the NCCLS publication entitled METHODS FOR DILUTION ANTIMICROBIAL SUSCEPTIBILITY TESTS (1991), which is incorporated herein by reference.

Aliquots of antimicrobial agents and test compounds are prepared in phosphate buffered saline (PBS) at pH 7.2. Tween 20 or DMSO is used as a solubilizing vehicle as needed. Standard methods of vortexing, sonicating and gentle heat are used to facilitate solubilizing of the test agent. Typically, the concentration of the stock antimicrobial agent solution is 10× that of the highest concentration tested. A 1.28 mg/mL stock solution is used with a subsequent highest working concentration of 128 µg/ml. Serial two-fold dilutions are done through less than or equal to 0.25 µg/mL. Each drug level is tested in duplicate. Two-fold drug dilutions are done in sterile 50 mL tubes with a final drug volume of 5 mL. Upon the addition of 45 mL of molten agar, a 10-fold dilution results. Two, 265 mL plates are then poured into 15×150 mm square Petri plates with grids and allowed to harden.

Example 8

In vivo modeling: Efficacy

Efficacy of potentiators can be tested in a mucin-enhanced acute mouse peritonitis model. In the example of Methicillin Potentiation, $5 \times 10^5$ cfu MRSA in 10% hog gastric mucin will be administered intraperitoneally to mice. Treatment with potentiator alone, potentiator plus a β-lactam, or β-lactam alone is accomplished subcutaneously or orally, as appropriate to the potentiator's physical chemistry properties. Initial studies use high doses of both antibacterial agent and potentiator. The optimal ratio of antibacterial agent to potentiator used is determined in subsequent studies, with initial ratios inferred from standard checkerboard assays in which both the concentration of potentiator and the concentration of the antibacterial agent are varied.

Alternatively, the efficacy of potentiators can be tested in a mouse thigh model. For this test neutropenia is induced in test mice by the injection of cyclophosphamide, with cyclophosphamide dosing similar to that described in Collins et al., *J. Infect. Dis.* 8 (Supp. 4) :S420–S425 (1986). That dosing used cyclophosphamide in isotonic saline, injected IP on days 0, 2, and 4 at 125 mg/kg (cyclophosphamide/mouse body weight). The neutropenia persists for approximately three days following the last injection.

The neutropenic mice are injected intramuscularly in a thigh with approximately $5\times10^5$ cfu MRSA (or other appropriate bacterium). After allowing the bacteria to grow in the thigh for a period of time appropriate for the bacterium used (typically in the range of 1 to 24 hours), the mouse is treated with a potentiator, a combination of a potentiator and an antibacterial agent, or an antibacterial agent alone, with the route of administration appropriate for the chemistry of the potentiator and antibacterial agent used. Dosages are determined in the manner described above for the peritonitis model above. (For a description of the use of the mouse thigh model, see B. Vogelman et al., *J. Infect. Dis.* 157:287–298 (1988).)

Example 9

Potentiation of Other Antibacterial Agents with Larixol Acetate

The procedures used in Examples 1–3 to determine potentiation activity, and MIC reduction have been carried out using larixol acetate as the test compound and various antibacterial agents in place of methicillin. These antibacterial agents include other β-lactams including, e.g., four penicillins, ampicillin, cloxacillin, oxacillin, and piperacillin; cephalosporins and other cephems including cefaclor, cefamandole, cefazolin, cefoperazone, cefotaxime, cefoxitin, ceftazidime, ceftriaxone, and cephalothin; the carbapenem imipenem; the glycopeptide vancomycin; and the aminoglycoside gentamicin. The results are shown in FIG. 2. For some β-lactams the potentiator induced a MIC reduction to less than $10^{-3}$ of the MIC for the antibacterial agent in the absence of the potentiator. Such determinations of MIC reduction can also appropriately be performed using any of a variety of other antibacterial agents, including, but not limited to, amoxicillin, cefalexin, cefonicid, mezlocillin, azlocillin, loracarbef, fluoxacillin, dicloxacillin, cefmenoxime, cefotiam, cefotetan, meropenem, and biapenem.

Example 10

Ampicillin Potentiation Screen in *Enterococcus faecium*

The ampicillin potentiation screen is another embodiment of the potentiation screen described for the methicillin potentiation screen in MRSA. Compounds identified as having potentiator activity in this screen must meet the same criteria as described under the methicillin potentiation screen, however, ampicillin is substituted for methicillin and *Enterococcus faecium* or *Enterococcus faecalis* or other ampicillin-resistant enterococcal species is substituted for MRSA (the description below will refer only to *E. faecium*). Other differences between the two embodiments are given in Methods, below.

The ampicillin potentiation screen is a high-throughput (96 well), whole cell assay in which compounds of unknown pharmacological activity are tested for their ability to induce an ampicillin-susceptible phenotype in highly ampicillin-resistant Enterococcus faecium (MIC of ampicillin>100 μg/ml). These highly ampicillin-resistant bacteria are grown in the presence of ampicillin and various test compounds. The concentration of ampicillin used is well below the MIC for the resistant cells, but higher than the MIC for the isogeneic susceptible cells. Therefore, resistant cells can grow in the presence of the ampicillin without test compound, but the growth of susceptible cells is repressed. Growth is assessed after 5–24 hours by turbidity. Compounds are also tested for intrinsic antibacterial activity in the absence of ampicillin. Compounds which repress *Enterococcus faecium* growth when used together with ampicillin, which show no, or only a little, intrinsic antibacterial activity, are considered potentiators.

Methods

When testing for a compound which will potentiate the action of ampicillin against resistant *Enterococcus faecium*, the cells are grown in the presence of 10 μg/ml test compound and 8 μg/ml ampicillin as follows:

A fresh inoculum of *E. faecium* cells are grown at 35° C. in Brain-Heart Infusion Broth (BHI) overnight and then diluted 1/50 in the same medium. After regrowth at 35° C. to an $OD_{600}$ of 0.2–0.4 (approximately 2 hours), the cells are diluted 1/800 in BHI. In a microtiter plate, 50 μl of this diluted culture are combined with 50 μl BHI containing 20 μg/ml test compound and 16 μg/ml ampicillin to give starting growth conditions of approximately $1\times10^5$ cfu/ml in BHI containing 10 μg/ml test compound and 8 μg/ml ampicillin. The plate is placed in a humidified 35° C. incubator for 24 hours, and cell growth or inhibition is read as turbidity ($OD_{600}$). Two positive and one negative controls for growth are cells grown in BHI, cells grown in BHI plus 8 μg/ml ampicillin (without test compound), and uninoculated BHI respectively. In order to be carried forward, a compound must significantly inhibit growth (equal to or less than 50% of the growth of the positive control with ampicillin, corrected for background) in this assay. Other methods are as described above for the methicillin potentiation screen with the appropriate substitutions of ampicillin and *E. faecium*.

Results

The evaluation results of two compounds which showed potentiation activity as assessed by criteria 1 and 2 (i.e. potentiation activity and little or no inhibition of target organism when used alone) is here described. The first compound reduces growth to 6% of positive control (in combination with ampicillin), while allowing up to 90% growth compared to positive control when used alone. The second compound reduces growth to 30% of the ampicillin-positive growth control. When used alone, some intrinsic activity is observed, but growth is still >75% of the positive growth control (without ampicillin).

Example 11

Glycopeptide Potentiation Screen

Plasmid-mediated glycopeptide resistance has been observed since 1986 (LeClercq et al., N.E.J.M. 319:157–161, 1988). Resistance mechanisms are genetically diverse, resulting in several resistance phenotypes (Arthur and Courvalin, Chemother. 37:1563–1571, 1993). There is a strong presumption in the scientific and medical communities that this resistance will be transferred from enterococcus and will appear in staphylococci. As with the other resistance phenomena described above, this resistance can be exploited in a potentiation screen to identify compounds that induce the glycopeptide-susceptible phenotype.

In order to identify such potentiators, compounds are tested for their ability to reduce growth of glycopeptide-resistant enterococci grown in the presence of sub-inhibitory levels of vancomycin or other glycopeptide. The concentration of glycopeptide is chosen to be sub-inhibitory to resistant strains, while inhibitory to susceptible strains. Growth is assessed after 5–24 hours by turbidity. Compounds are also tested for intrinsic antibacterial activity in the absence of glycopeptide. Compounds which repress the growth of vancomycin-resistant *Enterococcus faecium* when used together with glycopeptide, and which show no, or only slight, intrinsic activity are considered preliminary hits. Preliminary hits are subject to further criteria as outlined for the two screens described above. Variations of this screen use different glycopeptide-resistant enterococci strains that vary in their mechanism of resistance (e.g., VanA, VanB, VanC phenotypes) or other glycopeptide resistant genera, or glycopeptides other than vancomycin. Useful screening can be performed using glycopeptide resistant bacteria in which the resistance is induced by the presence of the glycopeptide.

Vancomycin Potentiation Protocol

Three screening protocols are described below, but alternative methods are clearly possible. Vancomycin is used for the glycopeptide potentiation assays described herein; teicoplanin could be used but was not, since it is not yet marketed in the United States.

Three different screening protocols have been used (VPS-8, VPS-D-ala, VPS-20) which differ in the concentration of vancomycin and in the presence or absence of a D-alanine supplement (See FIG. 7). Two of those screens have shown utility by providing preliminary hits, the VPS-20 screen and the VPS-D-Ala. They are used in conjunction with each other.

In the VPS-20 protocol, vancomycin is used at 20 ug/ml, test compounds are used at 10 ug/ml (this is not critical, a range could be used as well). The growth medium is Brain Heart Infusion broth however, any of a variety of media which will support growth of the specific bacterial strain can be used. The VPS-D-Ala screen uses 8 ug/ml of vancomycin and 50 mM D-alanine. This amino acid is added to feed the bacteria excess alanine, which allows the bacteria to incorporate the alanine in some cases instead of incorporating the (resistance causing) D-lactate in the pentapeptide termini of the cell wall precursor. The presence of this D-alanine supplement thus makes the assay less stringent.

The VPS-8 screen, using vancomycin at 8 ug/ml, has not shown hits when using *Enterococcus faecalis* VanA, probably because it is too difficult for the vancomycin to be effective when the MIC is so high in the test strain (512 ug/ml). In addition, in the bacterial strain used in the assays below, vancomycin induces the resistance mechanism. Since there is vancomycin in the test it is not surprising that hits have not been observed for this assay, since only a very potent potentiator would be able to significantly affect growth in this assay. However, it is likely that the VPS-8 protocol (or one with a similar glycopeptide concentration) will be useful in conjunction with bacterial strains in which the glycopeptide resistance is not induced by a glycopeptide, such as strains in which the resistance is constitutively expressed.

Detailed Procedure: VPS-20 and VPS-D-ala Assays

Inoculum Preparation:

Inoculate *E. faecalis* VanA strain in BHI broth (pick a few colonies into 3 ml BHI with 2.56 ug/ml vancomycin and grow O/N at 35° C. in a shaker rotating at 225 rpm.

Dilute the O/N culture 1:50 in BHI with 2.56 ug/ml vancomycin (0.5 ml±24.5 ml BHI) in a 125-ml flask, put back in the 35° C. shaker until the cells grow to early log phase (OD600 about 0.2, takes approximately 2 hrs). Make a 1:800 dilution of the log phase culture with BHI broth. 50 ul of these diluted cells will be used as the inoculum in the assay as described below. Add the inoculum after the other reagents.

Meanwhile, test the inoculum concentration and purity: Make 3 serial 10-fold dilutions of the inoculum in 0.2 ml BHI broth. Plate 100 ul on TSA agar plates (trypticase soy agar), incubate at 35° C. O/N, count the colonies to estimate the CFU/ml in the inoculum (it should be $10^4$–$10^5$ CFU/ml).

Reagent Preparation:

Make vancomycin stock at 50 mg/ml in ddH$_2$O. Filter sterilize with 0.2 um filter, and keep in the freezer. On the day of the assay, dilute vancomycin to 50 ug/ml (for VPS-20) or 54 ug/ml (for VPS-D-ala) in BHI broth.

Prepare D-alanine (Sigma) at 800 mM in ddH2O. Filter sterilize with 0.2 um filter.

The test compounds are from 0.1 mg/ml plates in 10% DMSO, 90% 50 mM HEPES, pH 7.3. Thaw at room temperature.

Preparation of Assay Plates and Toxicity Control Plates:

A. 20 ug/ml vancomycin screen (VPS-20):

1. Take 40 ul 50 ug/ml vancomycin in BHI to each well of the assay plate (Final volume will be 100 ul, making vancomycin concentration 20 ug/ml)
2. For each assay plate, prepare a toxicity control plate; instead of pipetting 40 ul of the vancomycin, use 40 ul of BHI broth in each well of the assay plate.

B. 8 ug/ml vancomycin +50 mM D-alanine Screen (VPS-D-ala):

3. Dilute 800 mM D-alanine to 200 mM in BHI broth, take 25 ul of the 200 mM D-alanine to both the assay plate and the toxic control plate.
4. Take 15 ul of 54 ug/ml vancomycin in BHI to each well of the assay plate (Final volume will be 100 ul, making vancomycin concentration 8 ug/ml)
5. For each assay plate, prepare a toxicity control plate; instead of pipetting 15 ul of the vancomycin, use 15 ul of BHI broth in each well of the assay plate.
6. Take 10 ul/well of the test compounds to the assay plates and the toxicity control plates. Do this in perfect register in the microtiter plates (change tips), and work using sterile technique (Final concentration will be 10 ug/ml test compounds, 1% DMSO). This must be done with separate tips, in perfect register.
7. Add 10 ul of 10% DMSO, 90% 50 mM HEPES, pH 7.3 in columns 1 and 12 in each plates.
8. Inoculate all wells in columns 2 to 11 with 50 ul 1/800 diluted log phase culture (prepared as indicated above). Use 50 ul sterile BHI instead of inoculum for the negative growth controls in well A–D in columns 1 and well E–H in columns 12. Add 50 ul of inoculum to Wells E–H in columns 1 and wells A-D in columns 12 for the positive growth controls.
9. Controls could be set up with 200 mM D-alanine+ minimum of 20 ug/ml vancomycin (The checkerboard study showed that in the presence of 200 mM D-alanine, the MIC for vancomycin dropped from 512 ug/ml to 16 ug/ml). 25 ul of the 800 mM D-alanine, 15 ul of 134 ug/ml vancomycin, 10 ul of 10% DMSO, 90% 50 mM HEPES, pH 7.3, 50 ul of BHI broth (negative control) or the inoculum (positive control).

10. Replace lids with mylar tape, and carefully punch pinholes in the top of each well.
11. Place the microtiter plates in a humidified 35° C. incubator (Do not stack). Remove mylar lids and check the cell density (A600) in 21–24 hours using a microtiter plate reader. The plates will need to be agitated carefully to resuspend the cells before reading.

Controls:
1: 100 ul (20 ug/ml vancomycin in BHI broth, 200 mM D-alanine in BHI broth, 1% DMSO)
2: 50 ul (40 ug/ml vancomycin in BHI broth, 400 mM D-alanine in BHI broth, 2% DMSO)+50 ul inoculum
3: 50 ul (40 ug/ml vancomycin in BHI broth, 2% DMSO; or 16 ug/ml vancomycin +100 mM D-alanine in BHI broth, 2% DMSO)+50 ul inoculum
4: 100 ul (20 ug/ml vancomycin in BHI broth, 1% DMSO; or 8 ug/ml vancomycin +50 mM D-alanine in BHI broth, 1% DMSO)

Results:
The structures of three compounds which are preliminary hits for vancomycin potentiation using the VPS-20 and VPS-D-ala assays are shown in FIG. 8. As preliminary hits, each compound reduced bacterial growth in at least one of the assays, VPS-20 or VPS-D-ala.

The percent growth inhibition for each of the three compounds in each of the two assays is also shown in FIG. 8. For example, for the VPS-20 screen the first number (88) is percent inhibition in the assay, the second number (4) is percent intrinsic inhibition in the control. Hence N-benzyl thiosalicylamide is a very potent inhibitor in the assay and has little intrinsic activity. The other two hits (brazilin, 6-ethyl-7-[oxo-3-(1-pyrrolidino)]propyl-1,2,3,4-tetrahydro-1,1,4,4-tetramethylnapthalene) were positive, but less than N-benzyl thiosalicylamide, and showed some intrinsic activity against the control cells (e.g., 32% for brazilin in the VPS-20 assay).

Two of the three compounds (brazilin and 6-ethyl-7-[oxo-3-(1-pyrrolidino)]propyl-1,2,3,4-tetrahydro-1,1,4,4-tetramethylnaphthalene) have been examined for synergy with vancomycin. A dose range study showed synergy for these compounds against Enterococcus faecalis VanA and E. faecalis VanB phenotypes (FIGS. 9a & 9b). Thus, the preliminary assay and synergy results demonstrate that the glycopeptide potentiation screen, as described, is effective in screening for possible potentiators of vancomycin, but clearly the assays can be altered to provide other particular embodiments. Two examples of reasons for alterations are for further optimization, and for modification for use with other bacterial strains or species.

Other Embodiments

Although specific examples are provided above, those in the art will recognize that potentiator screening assays can be performed on other test organisms (strains and species) exhibiting antibacterial agent resistance. Such organisms include other strains of MRSA such as COL, SRM551, and SRM401 (Murakami and Tomasz, *J. Bact.*171: 874–879 (1989)). They also include other Staphylococcus species such as *S. epidermidis, S. haemolyticus* and *S. simulans*, other Enterococcus species, as well as species and strains from other genera.

In addition, the screening assays can also be used to detect potentiators for antibacterial agents other than the β-lactam and glycopeptide antibacterial agents shown in the examples, by utilizing bacteria resistant to other antibacterial drugs and substituting the corresponding antibacterial agent for those antibacterial agents named above. Thus, such other antibacterial agents can include e.g., other β-lactam, β-lactam mimic, glycopeptide, macrolide, quinolone, tetracycline, and aminoglycoside agents.

The embodiments herein described are not meant to be limiting to the invention. Those of skill in the art will appreciate the invention may be practiced by using numerous compounds and by numerous methods all within the breadth of the claims.

Other embodiments are within the following claims.

What is claimed is:

1. A method for treating a bacterial infection in a mammal, comprising administering to a mammal suffering from said infection an antibacterial agent and a potentiating compound, wherein said potentiating compound increases the susceptibility of a bacterium to said antibacterial agent, and wherein said potentiating compound has a structure of Structure 2, namely:

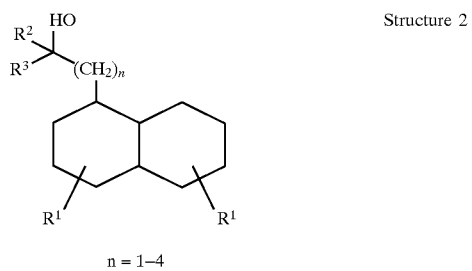

n = 1–4 wherein each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

2. The method of claim 1, wherein said antibacterial agent is selected from the group consisting of glycopeptides, macrolides, quinolones, tetracyclines, and aminoglycosides.

3. The method of claim 1, wherein said antibacterial agent is a β-lactam.

4. The method of claim 3, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

5. A method for treating a bacterial infection in a mammal, comprising administering to a mammal suffering from said infection an antibacterial agent and a potentiating compound, wherein said potentiating compound increases the susceptibility of a bacterium to said antibacterial agent, and wherein said potentiating compound has a structure of Structure 3, namely:

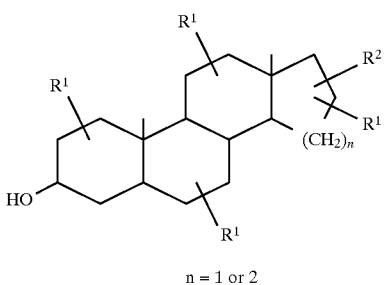

n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, or hydroxyalkyl, and $R^2$ may form another 5- or 6-member ring, but no more than one substituent, $R^1$ or $R^2$, is alkoxy, acyloxy, or hydroxyalkyl, and $R^1$ on the ring substituted with $R^2$ is not acyloxy.

6. The method of claim 5, wherein said antibacterial agent is selected from the group consisting of glycopeptides, macrolides, quinolones, tetracyclines, and aminoglycosides.

7. The method of claim 5, wherein said antibacterial agent is a β-lactam.

8. The method of claim 7, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

9. A method for prophylactic treatment of a mammal, comprising administering to a mammal at risk of a bacterial infection an antibacterial agent and a potentiating compound, wherein said potentiating compound increases the susceptibility of a bacterium to said antibacterial agent; and wherein said potentiating compound has a structure of Structure 2, namely:

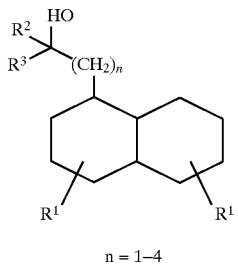

n = 1–4 wherein each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

10. The method of claim 9, wherein said antibacterial agent is selected from the group consisting of glycopeptides, macrolides, quinolones, tetracyclines, and aminoglycosides.

11. The method of claim 10, wherein said antibacterial agent is a β-lactam.

12. The method of claim 11, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

13. A method for prophylactic treatment of a mammal, comprising administering to a mammal at risk of a bacterial infection an antibacterial agent and a potentiating compound, wherein said potentiating compound increases the susceptibility of a bacterium to said antibacterial agent; and wherein said potentiating compound has a structure of Structure 3, namely:

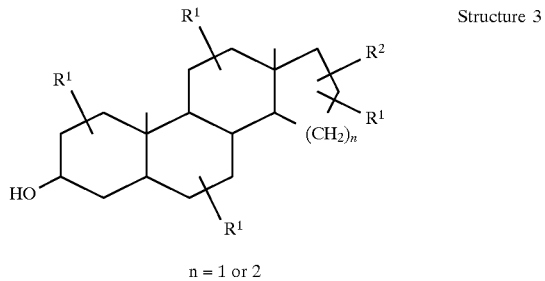

n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, or hydroxyalkyl, and $R^2$ may form another 5- or 6-member ring, but no more than one substituent, $R^1$ or $R^2$, is alkoxy, acyloxy, or hydroxyalkyl, and $R^1$ on the ring substituted with $R^2$ is not acyloxy.

14. The method of claim 13, wherein said antibacterial agent is selected from the group consisting of glycopeptides, macrolides, quinolones, tetracyclines, and aminoglycosides.

15. The method of claim 13, wherein said antibacterial agent is a β-lactam.

16. The method of claim 15, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

17. A pharmaceutical composition effective for treatment of an infection of a mammal by resistant bacteria when administered in conjunction with an antibacterial agent, comprising a carrier and a potentiator compound, wherein said potentiator compound has a structure of Structure 2, namely:

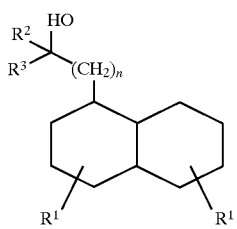

Structure 2 wherein n is 2, 3, or 4, each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

18. A pharmaceutical composition effective for treatment of an infection of a mammal by resistant bacterial when administered in conjunction with an antibacterial agent, comprising a carrier and a potentiator compound, wherein said potentiator compound has a structure of Structure 3, namely:

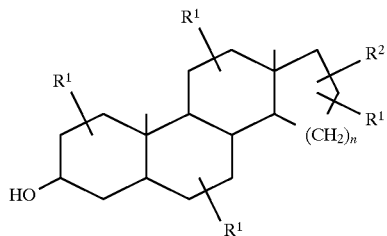

Structure 3 n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, or hydroxyalkyl, and $R^2$ may form another 5- or 6-member ring, but no more than one substituent, $R^1$ or $R^2$, is alkoxy, acyloxy, or hydroxyalkyl, and $R^1$ on the ring substituted with $R^2$ is not acyloxy.

19. A pharmaceutical composition effective for treatment of an infection of a mammal by resistant bacteria, comprising a potentiator compound and an antibacterial agent, wherein said potentiator compound has a structure of Structure 2, namely:

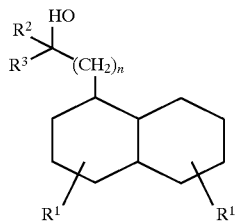

Structure 2 n = 1–4 wherein each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

20. The composition of claim 19, wherein said antibacterial agent is selected from the group consisting of glycopeptides, macrolides, quinolones, tetracyclines, and aminoglycosides.

21. The composition of claim 19, wherein said antibacterial agent is a β-lactam.

22. The composition of claim 21, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

23. A pharmaceutical composition effective for treatment of an infection of a mammal by resistant bacteria, comprising a potentiator compound and an antibacterial agent, wherein said potentiator compound has a structure of Structure 3, namely:

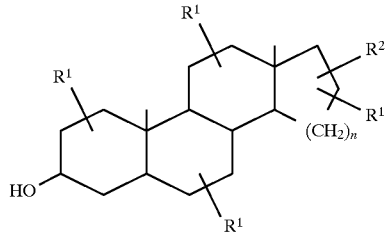

Structure 3 n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, or hydroxyalkyl, and $R^2$ may form another 5- or 6-member ring, but no more than one substituent, $R^1$ or $R^2$, is alkoxy, acyloxy, or hydroxyalkyl, and $R^1$ on the ring substituted with $R^2$ is not acyloxy.

24. The composition of claim 23, wherein said antibacterial agent is selected from the group consisting of glycopeptides, macrolides, quinolones, tetracyclines, and aminoglycosides.

25. The composition of claim 23, wherein said antibacterial agent is a β-lactam.

26. The composition of claim 25, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

27. A formulation comprising an antibacterial agent, a potentiator compound, and a carrier, wherein said potentiator compound has a structure of Structure 2, namely:

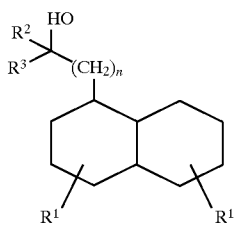

Structure 2 n = 1–4 wherein each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

28. The formulation of claim 27, wherein said antibacterial agent is selected from the group consisting of glycopeptides, macrolides, quinolones, tetracyclines, and aminoglycosides.

29. The formulation of claim 27, wherein said antibacterial agent is a β-lactam.

30. The formulation of claim 29, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

31. A formulation comprising an antibacterial agent, a potentiator compound, and a carrier, wherein said potentiator compound has a structure of Structure 3, namely:

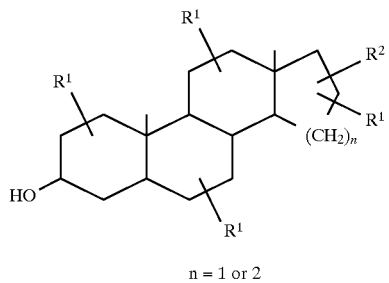

Structure 3 n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, or hydroxyalkyl, and $R^2$ may form another 5- or 6-member ring, but no more than one substituent, $R^1$ or $R^2$, is alkoxy, acyloxy, or hydroxyalkyl, and $R^1$ on the ring substituted with $R^2$ is not acyloxy.

32. The formulation of claim 31, wherein said antibacterial agent is selected from the group consisting of glycopeptides, macrolides, quinolones, tetracyclines, and aminoglycosides.

33. The formulation of claim 31, wherein said antibacterial agent is a β-lactam.

34. The formulation of claim 33, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

35. A method of suppressing growth of a bacterium resistant to an antibacterial agent comprising contacting said bacterium with a potentiator compound in the presence of a concentration of antibacterial agent below the MIC of said resistant bacterium, wherein said potentiator compound is a cyclic terpene.

36. The method of claim 35, wherein said antibacterial agent is selected from the group consisting of glycopeptides, macrolides, quinolones, tetracyclines, and aminoglycosides.

37. The method of claim 35, wherein said antibacterial agent is a β-lactam.

38. The method of claim 37, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

39. A method of suppressing growth of a bacterium resistant to an antibacterial agent comprising contacting said bacterium with a potentiator compound in the presence of a concentration of antibacterial agent below the MIC of said resistant bacterium, wherein said potentiator compound has a structure of Structure 2, namely:

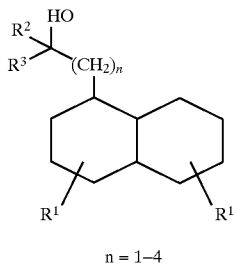

Structure 2 n = 1–4 wherein each ring independently is aromatic or aliphatic, if aliphatic the individual bonds in a ring are single or double bonds, and the ring structure is optionally substituted with one or more substituents, $R^1$, wherein each $R^1$ independently is alkyl, alkoxy, acyloxy, or halogen, but no more than one substituent, $R^1$, is alkoxy or acyloxy, and wherein $R^2$ and $R^3$ are independently H, alkyl, or alkenyl, and $R^2$ may be alkoxy, hydroxyalkyl, or acyloxy, and either $R^2$ or $R^3$ may form another 5- or 6-member ring, but no more than one substituent, $R^1$ or $R^2$, is alkoxy, acyloxy, or hydroxyalkyl.

40. The method of claim 39, wherein said antibacterial agent is selected from the group consisting of glycopeptides, macrolides, quinolones, tetracyclines, and aminoglycosides.

41. The method of claim 39, wherein said antibacterial agent is a β-lactam.

42. The method of claim 41, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

43. A method of suppressing growth of a bacterium resistant to an antibacterial agent comprising contacting said bacterium with a potentiator compound in the presence of a concentration of antibacterial agent below the MIC of said resistant bacterium, wherein said potentiator compound has a structure of Structure 1, namely:

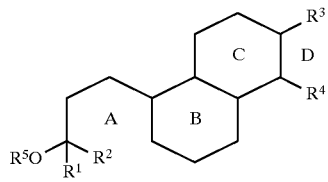

Structure 1 wherein $R^1$ and $R^2$ are independently H, alkyl, or alkenyl, and $R^1$ or $R^2$ may be methylene or methine attached to ring B to form another ring A;

$R^3$ and $R^4$ are independently H, alkyl, halogen, alkoxy, acyloxy, oxo, or together may be joined to form a 5- or 6-membered ring D, and ring D may have fused to it a 5- or 6-membered ring E;

$R^5$ is H or alkyl;

rings A, B, C, D, and E are independently aliphatic or aromatic, if aliphatic the individual bonds may be single or double bonds, the ring junctures may be cis or trans, and the rings may optionally be substituted with alkyl with one to six carbon atoms, halogen, acyloxy, alkoxy, or oxo.

44. The method of claim 43, wherein said antibacterial agent is selected from the group consisting of glycopeptides, macrolides, quinolones, tetracyclines, and aminoglycosides.

45. The method of claim 43, wherein said antibacterial agent is a β-lactam.

46. The method of claim 45, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

47. A method of suppressing growth of a bacterium resistant to an antibacterial agent comprising contacting said bacterium with a potentiator compound in the presence of a concentration of antibacterial agent below the MIC of said resistant bacterium, wherein said potentiator compound has a structure of Structure 3, namely:

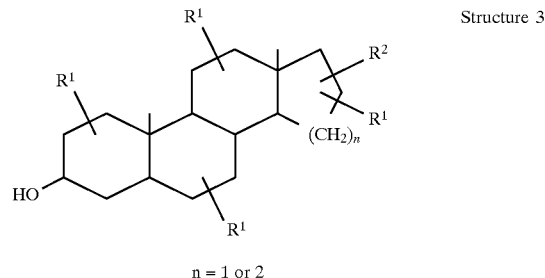

Structure 3 n = 1 or 2 wherein each ring independently is aromatic or aliphatic, if aliphatic the individual bonds in a ring are single or double bonds, and the ring structure is optionally substituted with one or more substituents, $R^1$, wherein each $R^1$ independently is alkyl with one to six carbon atoms, alkoxy, acyloxy, or halogen, but no more than one substituent, $R^1$, is alkoxy or acyloxy, and wherein $R^2$ is independently H, alkyl, alkenyl, alkoxy, hydroxyalkyl, or acyloxy, and $R^2$ may form another 5- or 6-member ring, but no more than one substituent, $R^1$ or $R^2$, is alkoxy, acyloxy, or hydroxyalkyl.

48. The method of claim 47, wherein said antibacterial agent is selected from the group consisting of glycopeptides, macrolides, quinolones, tetracyclines, and aminoglycosides.

49. The method of claim 47, wherein said antibacterial agent is a β-lactam.

50. The method of claim 49, wherein said β-lactam is selected from the group consisting of ampicillin, amoxicillin, cloxacillin, flucloxacillin, methicillin, oxacillin, piperacillin, azlocillin, mezlocillin, cefaclor, cefalexin, cefamandole, cefazolin, cefonicid, cefoperazone, cefotaxime, cefoxitin, ceftazidime, cefpirome, ceftriaxone, cephalothin, ceftibuten, cefixime, cefpodoxime, loracarbef, imipenem and meropenem.

51. The method of claim 5, wherein neither $R^1$ nor $R^2$ on the ring substituted by $R^2$ is alkoxy.

52. The method of claim 13, wherein neither $R^1$ nor $R^2$ on the ring substituted by $R^2$ is alkoxy.

53. The pharmaceutical composition of claim 18, wherein neither $R^1$ nor $R^2$ on the ring substituted by $R^2$ is alkoxy.

54. The pharmaceutical composition of claim 23, wherein neither $R^1$ nor $R^2$ on the ring substituted by $R^2$ is alkoxy.

55. The formulation of claim 31, wherein neither $R^1$ nor $R^2$ on the ring substituted by $R^2$ is alkoxy.

* * * * *